United States Patent [19]

Harpold et al.

[11] Patent Number: 5,436,128
[45] Date of Patent: Jul. 25, 1995

[54] ASSAY METHODS AND COMPOSITIONS FOR DETECTING AND EVALUATING THE INTRACELLULAR TRANSDUCTION OF AN EXTRACELLULAR SIGNAL

[75] Inventors: Michael M. Harpold, El Cajon; Paul Brust, San Diego, both of Calif.

[73] Assignee: Salk Institute Biotechnology/Industrial Associates, La Jolla, Calif.

[21] Appl. No.: 962,238

[22] Filed: Jan. 27, 1993

Related U.S. Application Data

[63] Continuation-in-part of Ser. No. 563,751, Aug. 7, 1990.

[51] Int. Cl.[6] .................... C12Q 1/68; C12N 15/63; G01N 33/48; G01N 33/00
[52] U.S. Cl. .................... 435/6; 435/172.3; 435/240.1; 436/63; 436/94; 935/36; 935/39; 935/41
[58] Field of Search ............... 435/6, 172.3, 240.1; 436/63, 94; 935/36, 39, 41

[56] References Cited

U.S. PATENT DOCUMENTS

| | | | |
|---|---|---|---|
| 4,859,609 | 8/1989 | Dull et al. | 436/501 |
| 4,981,784 | 1/1991 | Evans et al. | 435/6 |
| 5,071,773 | 12/1991 | Evans et al. | 436/501 |
| 5,091,518 | 2/1992 | Sucov et al. | 536/23.2 |

FOREIGN PATENT DOCUMENTS

| | | |
|---|---|---|
| 0325849 | 8/1989 | European Pat. Off. |
| 8803168 | 5/1988 | WIPO |
| 89/09834 | 10/1989 | WIPO |
| 8909834 | 10/1989 | WIPO |
| 9106677 | 5/1991 | WIPO |
| 91/15602 | 10/1991 | WIPO |

OTHER PUBLICATIONS

Collins et al., Proc. Natl. Acad. Sci., USA, 86 (Jul. 1989), pp. 4853–4857.
Herschman, TIBS 14, (Nov. 1989), 455–458.
Allard, et al., "Sequence of the gene encoding the human M1 muscarinic acetylcholine receptor," *Nucl. Acids. Res.*, 15:10604 (1987).
Subramani, et al., "Expression of the mouse dihydrofolate reductase complementary deoxyribonucleic acid in simian virus 40," *Mol. Cell Biol.*, 1:854–864 (1981).
Deschamps, et al., "Identification of a transcriptional enchancer element upstream from the proto-oncogen fos," *Science*, 230:1174–1177 (1985).
Michel, et al., "PC12 phaeochromocytoma cells contain an atypical muscarinic receptor binding site," *Br. J. Pharmacol.*, 97:914–920 (1989).
Lambert, et al., "Muscarinic receptor binding characteristics of a human neuroblastoma SK-N-SH and its clones SH-SY5Y and SH-EP1," *Eur. J. Pharmacol.*, 165:71–77 (1989).
Serra, et al., "The intact human neuroblastoma cell (SH-SY5Y) exhibits high-affinity [$^3$H]pirenzepine binding associated with hydrolysis of phosphatidylinositols," *J. Neurochem.*, 50:1513–1521 (1986).
Serra, et al., "Phorbol esters alter muscarinic receptor (List continued on next page.)

*Primary Examiner*—Mindy B. Fleisher
*Attorney, Agent, or Firm*—Brown, Martin, Haller & McClain

[57] ABSTRACT

Transcription based assays that identify extracellular signals that modulate the activity of cell surface proteins are provided. Extracellular signals are identified by measuring the amount of transcription of a reporter gene in a recombinant cell that expresses the cell surface protein and contains DNA encoding the reporter gene under the transcriptional control of a promoter that is regulated, directly or indirectly, by the cell surface protein. The assays, provide a means for identifying potential pharmaceutical compounds that can be used to treat disease by virtue of their agonistic or antagonistic effects on the cell surface protein. Recombinant cells that express cell surface receptors and that contain reporter gene constructs that include transcriptional regulatory elements that are responsive to the activity of the cell surface receptors are also provided.

48 Claims, No Drawings

OTHER PUBLICATIONS binding and inhibit polyphosphoinositide breakdown in human neuoblastoma (SH–SY5Y) cells," *Biochem. Biophys. Res. Comm.*, 140(1):160–166 (1986).

Peralta, et al., "Differential regulation of PI hydrolysis and adenylyl cyclase by mascarinic receptor subtypes," *Nature*, 334:434–437 (1988).

Horwitz, et al., "Muscarinic receptor stimulation increases inositol–phospholipid metabolism and inhibits cyclic AMP accumulation in PC12 cells," *J. Neurochem.*, 53:197–204 (1989).

Bonner, et al., "Cloning and expression of the human and rat m5 muscarinic acetylcholine receptor genes," *Neuron*, 1:403–410 (1988).

Wada, et al., "Functional expression of a new pharmacological subtype of brain nicotinic acetylcholine receptor," *Science*, 240:330–334 (1988).

Boulter, et al., "Isolation of a cDNA clone coding for a possible neural nicotinic acetylcholine receptor α–subunit," *Nature*, 319:368–374 (1986).

Goldman, et al., "Members of a nicotinic acetylcholine receptor gene family are expressed in different regions of the mammalian central nervous system", *Cell*, 48:965–973 (1987).

Boulter, et al., "α3, α5, and β4: Three members of the rat neuronal nicotinic acetylcholine receptor–related gene family form a gene cluster," *J. Biol. Chem.*, 265:4472–4482 (1990).

Deneris, et al., "Primary structure and expression of β2: A novel subunit of neuronal nicotinic acetylcholine receptors," *Neuron*, 1:45–54 (1988).

Deneris, et al., "β3: A new member of nicotinic acetylcholine receptor gene family is expressed in brain," *J. Biol. Chem.*, 264:6268–6272 (1989).

Duvoisin, et al., "The functional diversity of the neuronal nicotinic acetylcholine receptors is increased by a novel subunit: β4," *Neuron*, 3:487–496 (1989).

Schofield, et al., "Sequence and functional expression of the $GABA_A$ receptor shows a ligand–gated receptor super–family," *Nature*, 328:221–227 (1987).

Levitan, et al., "Structural and functional basis for $GABA_A$ receptor heterogeneity," *Nature*, 335:76–79 (1988).

Pritchett, et al., "Importance of a novel $GABA_A$ receptor subunit for benzodiazepine pharmacology," *Nature*, 338:582–585 (1989).

Ymer, et al., "$GABA_A$ receptor β subunit heterogeneity: functional expression of cloned cDNAs," *EMBO J.*, 8:1665–1670 (1989).

Shivers, et al.; "Two novel $GABA_A$ receptor subunits exist in distinct neuronal subpopulations," *Neuron*, 3:327–337 (1989).

Hollmann, et al., "Cloning by functional expression of a member of the glutamate receptor family," *Nature*, 342:643–648 (1989).

Frielle, et al., "Cloning of the cDNA for the human $β_1$–adrenergic receptor," *PNAS*, 84:7920–7924 (1987).

Kobilka, et al., "Cloning, sequencing, and expression of the gene coding for the human platelet $α_2$–adrenergic receptor," *Science*, 238:650–656 (1987).

Dixon, et al., "Cloning of the gene and cDNA for mammalian β–adrenergic receptor and homology with rhodopsin," *Nature*, 321:75–79 (1986).

Stormann, et al., "Molecular cloning and expression of a dopamine D2 receptor from human retina," *Molec. Pharm.*, 37:1–6 (1990).

Bunzow, et al., "Cloning and expression of a rat $D_2$ dopamine receptor cDNA," *Nature*, 336:783–787 (1988).

Johnson, et al., "Expression and structure of the human NGF receptor," *Cell*, 47:545–554 (1986).

Kobilka, et al., "An intronless gene encoding a potential member of the family of receptors coupled to guanine nucleotide regulatory proteins," *Nature*, 329:75–79 (1987).

Julius, et al., "The 5HT2 receptor defines a family of structurally distnict but functionally conserved serotonin receptors," *PNAS*, 87:928–932 (1990).

Julius, et al., "Molecular characterization of a functional cDNA encoding the serotonin 1c receptor," *Science*, 241:558–564 (1988).

Tanabe, et al., "Primary structure of the receptor for calcium channel blockers from skeletal muscle," *Nature*, 328:313–318 (1987).

Ellis, et al., "Sequence and expression of mRNAs encoding the $α_1$ and $α_2$ subunits of a DHP–sensitive calcium channel," *Science*, 241:1661–1664 (1988).

Ruth, et al., "Primary structure of the β subunit of the DHP–sensitive calcium channel from skeletal muscle," *Science*, 245:1115–1118 (1989).

Jay, et al., "Primary structure of the γ subunit of the DHP–sensitive calcium channel from skeletal muscle," *Science*, 248:490–492 (1990).

McKinnon, D., "Isolation of a cDNA clone coding for a putative second potassium channel indicates the existence of a gene family," *J. Biol. Chem.*, 264:8230–8236 (1989).

(List continued on next page.)

OTHER PUBLICATIONS

Tempel, et al., "Cloning of a probable potassium channel gene from mouse brain," *Nature*, 332:837–839 (1988).

Noda, et al., "Existence of distinct sodium channel messenger RNAs in rat brain," *Nature*, 320:188–192 (1986).

Kayano, et al., "Primary structure of rat brain sodium channel III deduced from the cDNA sequence," *FEBS Lett.*, 228:187–194 (1988).

Fink, et al., "The CGTCA sequence motif is essential for biological activity of the vasoactive intestinal peptide gene cAMP-regulated enhancer," *Proc. Natl. Acad. Sci.*, 85:6662–6666 (1988).

Montminy, et al., "Identification of a cyclic-AMP-responsive element within the rat somatostatin gene," *Proc. Natl. Acad. Sci.*, 83:6682–6686 (1986).

Comb, et al., "A cyclic AMP- and phorbol ester-inducible DNA element," *Nature*, 323:353–356 (1986).

Short, et al., "Characterization of the phosphoenolpyruvate carboxykinase (GTP) promoter-regulatory region," *J. Biol. Chem.*, 261:9721–9726 (1986).

Changelian, et al., "Structure of the NGFI-A gene and detection of upstream sequences responsible for its transcriptional induction by nerve growth factor," *Proc. Natl. Acad. Sci.*, 86:377–381 (1989).

Visvader, et al., "Two adjacent promotor elements mediate nerve growth factor activation of the c-fos gene and bind distinct nuclear complexes," *PNAS*, 85:9474–9478 (1988).

Verma, et al., "Proto-Oncogene fos: Complex but versatile regulation," *Cell*, 51:513–514 (1987).

Sheng, et al., "The regulation and function of c-fos and other immediate early genes in the nervous system," *Neuron*, 4:477–485 (1990).

Lamb, et al., "Demonstration in living cells of an intragenic negative regulatory element within the rodent c-fos gene," *Cell*, 61:485–496 (1990).

Alton and Vapnek, "Nucleotide sequence analysis of the chloramphenicol resistance transposon Tn9," *Nature*, 282:864–869 (1979).

deWet, et al., "Firefly luciferase gene: structure and expression in mammalian cells," *Mol. Cell. Biol.*, 7:725–737 (1987).

Engebrecht and Silverman, "Identification of genes and gene products necessary for bacterial bioluminescence," *PNAS*, 81:4154–4158 (1984).

Baldwin, et al., "Cloning of the luciferase structural genes from *Vibrio harveyi* and expression of bioluminescence in *Escherichia coli*," *Biochemistry*, 23:3663–3667 (1984).

Toh, et al., "Isolation and characterization of a rat liver alkaline phosphatase gene," *Eur. J. Biochem.*, 182:231–237 (1989).

Alam et al., "Reporter genes: Application to the study of mammalian gene transcription," *Analytical Biochemistry*, 188:245–254 (1990).

Blanchard et al., "The regulatory strategies of c-myc and c-fos proto-oncogenes share some common mechanisms," *Biochemie*, 70:877–884 (1988).

Bonnieu et al., "Requirements for c-fos mRNA down regulation in growth stimulated murine cells," *Oncogene*, 4:881–888 (1989).

Bouche, "Basic fibroblast growth factor enters the nucleolus and stimulates the transcription of ribosomal genes in ABAE cells undergoing $G_0 \rightarrow G_1$ transition," *Proc. Natl. Acad. Sci. USA*, 84:6770–6774 (1987).

Claudio et al., "Genetic reconstitution of functional acetylcholine receptor channels in mouse fibroblasts," *Science*, 238:1688–1694 (1987).

Curran et al., "Barium modulates c-fos expression and post-translational modification," *Proc. Natl. Acad. Sci. USA*, 83:8521–8524 (1986).

Curran et al., "FBJ murine osteosarcoma virus: Identification and molecular cloning of biologically active proviral DNA," *J. Virology*, 44(2):674–682 (1982).

Devreotes, P., "*Dictyostelium discoideum*: A model system for cell-cell interactions in development," *Science*, 245:1054–1058 (1989).

Firtel et al., "G protein linked signal transduction pathways in development: Dictyostelium as an experimental system," *Cell*, 58:235–239 (1989).

Goyal, R., "Muscarinic receptor subtypes," *New England Journal of Medicine*, 321(15):1022–1029 (1989).

Gilman, A., "G proteins: Transducers of receptor-generated signals," *Ann. Rev. Biochem.*, 56:615–649 (1987).

Gorman et al., "Recombinant genomes which express chloramphenicol acetyltransferase in mammalian cells," *Molecular and Cellular Biology*, 2(9):1044–1051 (1982).

Hall et al., "Expression and regulation of *Escherichia coli lacZ* gene fusions in mammalian cells," *J. Molecular and Applied Genetics*, 2:101–109 (1983).

Klein et al., "A chemoattractant receptor controls de- (List continued on next page.)

OTHER PUBLICATIONS velopment in *Dictyostelium discoideum*," *Science*, 241:1467–1472 (1988).

Noda et al., "Expression of functional sodium channels from cloned cDNA," *Nature*, 322:826–828 (1986).

Nordeen, S., "Luciferase reporter gene vectors for analysis of promoters and enhancers," *Bio Techniques*, 6(5):454–456 (1988).

Schilling et al., "Regulation of a fos–lacZ fusion gene: A paradigm for quantitive analysis of stimulus-transcription coupling," *Proc. Natl. Acad. Sci. USA*, 88:5665–5669 (1991).

Strader et al., "Structural basis of $\beta$–adrenegic receptor function," *FASEB Journal*, 3:1825–1832 (1989).

Urlaub et al., "Effect of gamma rays at the dihydrofolate reductase locus: Deletions and inversions," *Somatic Cell and Molecular Genetics*, 12(6):555–566 (1986).

Yeh et al., "Ultrastructural localization of a platelet–derived growth factor/v–sis–related protein(s) in cytoplasm and nucleus of simian sarcoma virus–transformed cells," *Proc. Natl. Acad. Sci. USA*, 84:2317–2321 (1987).

Young et al., "Isolation and characterization of a new cellular oncogene encoding a protein with multiple potential transmembrane domains," *Cell*, 45:711–719 (1986).

Zipser et al., "Mapping functional domains in the promoter region of the herpes thymidine kinase gene," *Proc. Natl. Acad. Sci. USA*, 78(10):6276–6280 (1981).

Cordon-Cardo et al., "The trk tyrosine protein kinase mediates the mitogenic properties of nerve growth factor and neurotrophin-3," *Cell*, 66:173–183 (1991).

Cotecchia et al., "Multiple second messenger pathways of $\alpha$–adrenergic receptor subtypes expressed in eukaryotic cells," *J. Biol. Chem.*, 265(1):63–69 (1990).

Deneris et al., "Pharmacological and functional diversity of neuronal nicotinic acetylcholine receptors," *TiPS*, 12:34–40 (1991).

Greenberg et al., "Stimulation of neuronal acetylcholine receptors induces rapid gene transscription," *Science*, 234:80–83 (1986).

Marullo et al., "Expression of human $\beta 1$ and $\beta 2$ adrenergic receptors in *E. coli* as a new tool for ligand screening," *Bio/Technology*, 7:923–927 (1989).

Mechti et al., "Sequence requirements for premature transcription arrest within the first intron of the mouse c-fos gene," *Mol. and Cell. Biol.*, 11(5):2832–2841 (1991).

Morgan et al., "Stimulus-transcription coupling in neurons: role of cellular immediate-early genes," *TINS*, 12(11):459–462 (1989).

Riabowol et al., "The catalytic subunit of cAMP-dependent protein kinase induces expression of genes containing cAMP-responsive enhancer elements," *Nature*, 336:83–86 (1988).

Sassone-Corsi et al., "Induction of proto-oncogene fos transcription through the adenylate cyclase pathway: characterization of a cAMP-responsive element," *Genes & Development*, 2:1529–1538 (1988).

ASSAY METHODS AND COMPOSITIONS FOR DETECTING AND EVALUATING THE INTRACELLULAR TRANSDUCTION OF AN EXTRACELLULAR SIGNAL

This application is a continuation-in-part of U.S. application Ser. No. 07/563,751, "ASSAY METHODS AND COMPOSITIONS USEFUL FOR MEASURING THE TRANSDUCTION OF AN INTRACELLULAR SIGNAL", to Harpold et al., filed on Aug. 7, 1990 and presently pending. This application is also related to U.S. application Ser. No. 07/620,250, "CALCIUM CHANNEL COMPOSITIONS AND METHODS" to , Ellis, et al., filed on Nov. 30, 1990 and now abandoned which is a continuation-in-part of U.S. application Ser. No. 07/176,899, to Ellis et al., filed on Apr. 4, 1988 and now abandoned, which in turn is a continuation-in-part of U.S. application Ser. No. 07/160,884, to Ellis et al., filed on Feb. 26, 1988 and now abandoned. U.S. applications Ser. Nos. 07/563,751, 07/620,250, 07/176,899, and 07/160,884 are incorporated herein in their entirety by reference thereto.

FIELD OF THE INVENTION

This invention relates to methods for identifying and evaluating thepharmacological properties of compounds that modulate the activities of cell surface proteins. This invention also relates to assays that assess the intracellular transduction of an extracellular signal using recombinant cells that are modified by introduction of a reporter gene under the control of a regulatable promoter and that express cell surface proteins whose activities are modulated by the extracellular signal and whose activities indirectly or directly regulate the expression of the promoter.

In particular, this invention relates to methods for detecting and assessing the ability of substances to act as agonists or antagonists of the activity of specific cell surface-localized receptors and ion channels.

BACKGROUND OF THE INVENTION

Eukaryotic organisms are composed of a multitude of cells, tissues and organs that must react rapidly and in a concerted manner to environmental stimuli, including external and internal stimuli, and intercellular and intracellular stimuli. In order for eukaryotic organisms to do so, mechanisms and biochemical pathways for achieving rapid and concerted responses have evolved. Cell surface proteins that span the cell membrane provide a means for achieving these responses.

Cell surface proteins permit intracellular transduction of extracellular signals. Cell surface proteins provide eukaryotic, as well as prokaryotic, cells a means to detect extracellular signals and transduce such signals intracellularly in a manner that ultimately results in a cellular response or a concerted tissue or organ response. Cell surface proteins, by intracellularly transmitting information regarding the extracellular environment via specific intracellular pathways induce an appropriate response to a particular stimulus. The response may be immediate and transient, slow and sustained, or some mixture thereof. By virtue of an array of varied membrane surface proteins, eukaryotic cells are exquisitely sensitive to their environment.

Extracellular signal molecules, such as growth hormones, vasodilators and neurotransmitters, exert their effects, at least in part, via interaction with cell surface proteins. For example, some extracellular signal molecules cause changes in transcription of target gene via changes in the levels of secondary messengers, such as cAMP. Other signals, indirectly alter gene expression by activating the expression of genes, such as immediate-early genes that encode regulatory proteins, which in turn activate expression of other genes that encode transcriptional regulatory proteins. For example, neuron gene expression is modulated by numerous extracellular signals, including neurotransmitters and membrane electrical activity. Transsynaptic signals cause rapid responses in neurons that occur over a period of time ranging from milleseconds, such as the opening of ligandgated channels, to seconds and minutes, such as second messenger-mediated events. Genes in neural cells that are responsive to transsynaptic stimulation and membrane electrical activity, include genes, called immediate early genes, whose transcription is activated rapidly, within minutes, and transiently (see, e.g., Sheng et al. (1990) Neuron 4: 477–485), and genes whose expression requires protein synthesis and whose expression is induced or altered over the course of hours.

Cell surface receptors and ion channels are among the cell surface proteins that respond to extracellular signals and initiate the events that lead to this varied gene expression and response. Ion channels and cell surface-localized receptors are ubiquitous and physiologically important cell surface membrane proteins. They play a central role in regulating intracellular levels of various ions and chemicals, many of which are important for cell viability and function.

Ion channels

Ion channels, which occur in a wide variety of organisms including fungi, plants and animals, are membrane spanning proteins that permit controlled entry of various ions into cells from the extracellular fluid. They function as gated pores in the cell membrane and permit the flow of ions down electrical or chemical gradients. Ion channels are classified on the basis of the ion that enters the cell via the channel.

Voltage gated ion channels

The modulation of transmembrane ion transport is often the primary event in the coupling of extracellular signals to intracellular events. Ion fluxes play essential roles in stimulus-secretion, stimulus-mitosis, stimulus-contraction (see, Curran et al. (1986) Proc. Natl. Acad. Sci. USA 83: 8521–8524). For example, the voltage-gating of calcium ions mediates the coupling of membrane depolarizing stimuli to transcriptional activation of c-fos gene. Elevation of intracellular calcium activates a calmodulin/calmodulin kinase system which induces c-fos expression.

Sodium channels

Sodium channels are responsible for the rising phase of the action potential in excitable cells. Sodium channels sense the transmembrane electric field and respond by opening a transmembrane ionic channel with specificity for $Na^+$.

Sodium channels have been studied and are well-characterized. Genes encoding the sodium channel, which is a glycoprotein, have been cloned from numerous sources have been used to express voltage-dependent sodium currents when injected into Xenopus oocytes (see, Noda et al. (1986) Nature 322: 826–828.

Calcium channels

Calcium channels are membrane-spanning, multi-subunit proteins that allow controlled entry of —$Ca^{+2}$— ions into cells from the extracellular fluid. All cells throughout the animal kingdom, and at least some bacterial, fungal and plant cells, possess one or more types of calcium channel.

The most common type of calcium channel is voltage-dependent. In a voltage-dependent channel, the "opening," to allow an influx of —$Ca^{+2}$— ions into the cells to begin, requires a depolarization to a certain level of the potential difference between the inside of the cell bearing the channel and the extracellular environment. The rate of influx of —$Ca^{+2}$— into the cell depends on this potential difference. All "excitable" cells in animals, such as neurons of the central nervous systems, peripheral nerve cells, and muscle cells, including those of skeletal muscles, cardiac muscles, and venous and arterial smooth muscles, have voltage-dependent calcium channels. Voltage-dependent calcium channels are thought to consist of two large subunits, of between about 130 and about 200 kilodaltons ("kD") in molecular weight, and a number (generally thought to be one to three) of different smaller subunits, of less than about 60 kD in molecular weight. At least one of the larger subunits and possibly some of the smaller are glycosylated. Some of the subunits are capable of being phosphorylated.

Voltage-dependent $Ca^{2+}$ channels regulate cellular function in excitable cells in many tissues, including brain and muscle cells. In excitable cells, these calcium channels mediate calcium-dependent depolarization and translate changes in membrane potential into an intracellular calcium signal that initiates specific cellular functions.

Calcium antagonists block ion flux through calcium channels and bind to distinct sites that are called the calcium antagonist receptor. $Ca^{2+}$ antagonist drugs bind specifically to $Ca^{2+}$ channels and are used to treat cardiovascular diseases. A variety of organic compounds, such as 1,4-dihydropyridine (DHP) derivatives are known to modulate ion flux through slow L-type calcium channels. The DHP-sensitive L-type calcium channel is a major entry pathway of extracellular $Ca^{2+}$.

Ligand-gated ion channels

Ligand-gated include nicotinic acetyl choline receptors, gamma-aminobutyric acid (GABA) receptors, and excitatory amino acid receptors.

Because of the health consequences of tobacco-derived nicotine, which is a neurotransmitter analog, the nicotinic acetylcholine receptor, which is expressed in the central nervous system, has been extensively studied. The nicotinic acetylcholine receptor is a ligand gated ion channel that binds the neurotransmitter, acetylcholine (ACh), and mediates synaptic transmission between nerve and muscle (see, e.g.., Claudio et al. (1987) science 238: 1688–1694). The receptor contains four polypeptide chains $\alpha$, $\beta$, $\tau$, and $\delta$, with a stoichiometry $\alpha_2\beta\tau\delta$. Cloning studies have identified several genes that encode the various subunit. The genes have distinct patterns of expression in various tissues, and, thus, form an array of receptor subtypes, which are pharmacologically and functionally diverse.

The PC12 cell line, which is a rat pheochromocytoma cell line, expresses both nicotinic and muscarinic acetylcholine receptors. The c-fos proto-oncogene and actin are induced within minutes after nicotinic agonists bind to their receptors on PC12 cells. The c-fos gene is also induced by treatment of PC12 cells with NGF. Induction by nicotine and NGF, however, exhibit different dependencies on the flux of extracellular —$Ca^{+2}$ into the cell. Induction by nicotine relies on flux of $Ca^{2+}$ channels; whereas, induction by NGF is independent of extracellular $Ca^{2+}$.

Cell Surface Receptors

Cell surface-localized receptors are membrane spanning proteins that bind extracellular signalling molecules or changes in the extracellular environment and transmit the signal via signal transduction pathways to effect a cellular response. Cell surface receptors bind circulating signal polypeptides, such as growth factors and hormones, as the initiating step in the induction of numerous intracellular pathways. Receptors are classified on the basis of the particular type of pathway that is induced. Included among these classes of receptors are those that bind growth factors and have intrinsic tyrosine kinase activity, such as the heparin binding growth factor (HBGF) receptors, and those that couple to effector proteins through guanine nucleotide binding regulatory proteins, which are referred to as G protein coupled receptors and G proteins, respectively.

G-coupled receptors

The G protein transmembrane signaling pathways consist of three proteins: receptors, G proteins and effectors. G proteins, which are the intermediaries in transmembrane signaling pathways, are heterodimers and consist of $\alpha$, $\beta$ and gamma subunits. Among the members of a family of G proteins the $\alpha$ subunits differ. Functions of G proteins are regulated by the cyclic association of GTP with the $\alpha$ subunit followed by hydrolysis of GTP to GDP and dissociation of GDP.

G protein coupled receptors are a diverse class of receptors that mediate signal transduction by binding to G proteins. Signal transduction is initiated via ligand binding to the cell membrane receptor, which stimulates binding of the receptor to the G protein. The receptor G protein interaction releases GDP, which is specifically bound to the G protein, and permits the binding of GTP, which activates the G protein. Activated G protein dissociates from the receptor and activates the effector protein, which regulates the intracellular levels of specific second messengers. Examples of such effector proteins include adenyl cyclase, guanyl cyclase, phospholipase C, and others.

G protein-coupled receptors, which are glycoproteins, are known to share certain structural similarities and homologies (see, e-g., Gilman, A.G., Ann. Rev. Biochem.56: 615–649 (1987), Strader, C.D. et al. The FASEB Journal 3: 1825–1832 (1989), Kobilka, B.K., et al. Nature 329:75–79 (1985) and Young et al. Cell 45: 711–719 (1986)). Among the G protein-coupled receptors that have been identified and cloned are the substance K receptor, the angiotensin receptor, the $\alpha$- and $\beta$-adrenergic receptors and the serotonin receptors. G protein-coupled receptors share a conserved structural motif. The general and common structural features of the G protein-coupled receptors are the existence of seven hydrophobic stretches of about 20–25 amino acids each surrounded by eight hydrophilic regions of variable length. It has been postulated that each of the seven hydrophobic regions forms a transmembrane $\alpha$ helix and the intervening hydrophilic regions form alternately intracellularly and extracellularly exposed loops. The third cytosolic loop between transmembrane domains five and six is the intracellular domain responsible for the interaction with G proteins.

G protein-coupled receptors are known to be inducible. This inducibility was originally described in lower eukaryotes. For example, the cAMP receptor of the cellular slime mold, Dictyostelium, is induced during differentiation (Klein et al., Science 241: 1467–1472 (1988). During the *Dictyostelium discoideum* differentiation pathway, cAMP, induces high level expression of its G protein-coupled receptor. This receptor transduces the signal to induce the expression of the other genes involved in chemotaxis, which permits multicellular aggregates to align, organize and form stalks (see, Firtel, R.A., et al. Cell 58: 235–239 (1989) and Devreotes, P., Science 245: 1054–1058 (1989)).

Growth Factors and Growth Factor Receptors

Polypeptide growth factors are modulators of cell proliferation and differentiation whose biological functions are mediated by the interaction of the growth factor with cell surface receptors and subsequent alterations in gene expression. Growth factors bind to specific receptors and appear to induce tyrosine phosphorylation and c-fos mRNA synthesis. In addition, at least some growth factors, such as platelet-derived growth factor (Yeh et al. (1987) *Proc. Natl. Acad. Sci. U.S.A.* 84: 2317) and heparin-binding growth factor-2 or basic fibroblast growth factor (see, Bouche et al. *Proc. Natl Acad. Sci.* U.S.A. 84: 6770), are translocated to the nucleus.

Activation of growth factor receptors by interaction with specific growth factors or with agents such as phorbol mistric acetate (PMA) activates protein kinase C, which is a family of ph0spholipid- and calcium-activated protein kinases. This activation results in the transcription of an array of proto-oncogene transcription factor encoding genes, including c-fos, c-myc and c-jun, proteases, protease inhibitors, including collagenase type I and plasminogen activator inhibitor, and adhesion molecules, including intercellular adhesion molecule I. Protein kinase C activation antagonizes growth factor activity by the rapid phosphorylation of growth factor receptors, which thereby decreases tyrosine kinase activity.

The interaction of nerve growth factor (NGF) with its receptor is typical of the array of responses such an extracellular signal induces. NGF is a polypeptide growth hormone that is necessary for differentiation and growth of the neural crest-derived sensory neuron. NGF binds to its specific cell surface receptor and is retrogradely transported to the cell body (see, Changelian et al. (1989) *Proc. Natl. Acad. Sci.* USA 86: 377–381). This initiates a cascade of intracellular events, culminating in a differentiated phenotype. PC12 cells, which are a rat pheochromocytoma cell line, are used as a model for the study of NGF-mediated differentiation. When treated with NGF, PC12 cells change from replicating adrenal-chromaffin-like cells to nonreplicating, electrically excitable sympathetic-neuron-like cells.

Concomitant with the phenotypic changes, there is induction and expression of specific genes. Binding of NGF to PC12 cells induces the immediate and rapid expression of certain genes, including the c-fos, NGF1-A and NGF1-B genes, which are referred to as early genes. Such early genes are believed to encode transcriptional regulators. The NGF-1A gene product contains tandemly repeated "zinc finger" domains that are characteristic of DNA-binding proteins, and the NGF1-B protein is homologous to members of the glucocorticoid receptor family and, thus, may function as a ligand-dependent modulator of transcription. The c-fos gene product, FOS appears to function as a transcriptional regulatory molecule.

The c-fos Gene and Related Genes

As discussed above, induction of expression of the c-fos gene is an event that is common to a number response pathways that are initiated by the activity of a variety of cell surface proteins.

The c-fos gene product, FOS, associates with the transcription activator JUN, which is the product of the c-jun gene, to form a complex that forms a transcription activation complex, AP-1. Transcription of both c-fos and c-jun is induced rapidly and transiently following stimulation. The induced mRNAs accumulate for 1–2 hours in the cytoplasm where the FOS and JUN proteins, which are short-lived, are translated and then translocated to the nucleus to form a heterodimeric protein complex that binds to the DNA regulatory element, AP-1 binding site.

The c-fos and c-jun genes are members of gene families that encode proteins that participate in the formation of heterodimeric complexes that interact with AP-1 binding sites. Transcription factor AP-1 is composed of several protein complexes whose concentrations change upon cell stimulation. These complexes specifically interact with a seven-base core nucleotide sequence motif, that is known to be a relatively common constituent of both positive and negative transcriptional regulatory elements and that is required for both basal and induced levels of gene expression The gene products, FOS and JUN cooperate in the regulation of target genes that underlie many cellular and adaptive responses to the environment. They are involved in a number of neurophysiological processes. For example, in PC12 cells FOS and JUN are induced by pharmacological, electrical, surgical and physiological stimuli, neurotrophic factors, neurotransmitters, depolarizing conditions and other agents that cause an influx of —$Ca^{2+}$— ions through voltage-dependent —$Ca^{2+}$— channels. These stimuli or signals cause c-fos induction via interaction with regulatory elements located-in the 5' flanking regions of the gene. Some extracellular stimuli also lead to changes in the extent and type of post-translation modification, which involves serine and threonine phosphorylation, of the FOS protein Thus, c-fos induction involves distinct second messenger pathways that act via separate regulatory elements and that differentially modify, the resulting gene product, FOS, which in turn interacts in different ways with differentially modified JUN protein. Therefore, a multitude of extracellular events induce expression of a small number of inducible proteins that form an array of protein complexes that can differentially bind to DNA regulatory elements that contain AP-1 binding sites.

Therefore, numerous cell surface proteins can act via overlapping transduction pathways and transduce extracellular signals that ultimately induce a variety of responses.

Cell surface proteins and pharmacological implications

Cell surface proteins, thus, play a major physiological role. There are many potential pharmacological uses for compounds that interact with and modulate the activity of cell surface proteins. For example, calcium channels, play a central role in regulating intracellular $Ca^{2+}$ levels, which influence cell viability and function. Intracellular $Ca^{2+}$ concentrations are implicated in a number of vital processes in animals, such as neurotransmitter release, muscle contraction, pacemaker activity, and secretion of hormones and other substances. Other cell surface molecules also play vital physiological roles; For example, the ligand-gated nicotinic acetylcholine receptor may mediate the harmful effects nicotine-derived tobacco. Growth factors and other mitogens that induce cell proliferation and cell growth are believed to play a role in tumor growth, which often carry identifiable cell surface receptors specific for growth factors and other extracellular signals.

A number of compounds useful in treating various diseases in animals, including humans, are thought to exert their beneficial effects by their interactions with cell surface proteins. Vasodilators and other cardiovascular drugs modulate the activities of voltage-dependent calcium channels. Many of these compounds bind to calcium channels and block, or reduce the rate of, influx of $Ca^{2+}$ into cells in response to depolarization of the cell membrane. Growth factors have been used to target toxins to tumor cells that express growth factor receptors.

An understanding of the pharmacology of compounds that interact with ion channels and/or cell-surface localized receptors, and the ability to rationally identify compounds that specifically interact with ion channels and/or cell surface-localized receptors to have desired therapeutic effects, have been hampered by the lack of rapid, effective means to identify those compounds which interact with specific ion channels and/or specific cell surface-localized receptors.

The availability of rapid, effective means to identify compounds which modulate or interact with ion channels and/or cell surface-localized receptors would enable the rapid screening of a large number of compounds to identify those candidates suitable for further, in-depth studies of therapeutic applications.

Therefore, it is an object of this invention to provide an assay for screening and identifying potential pharmaceutically effective compounds that specifically interact with and modulate the activity of cell surface proteins.

It is also an object of this invention to provide recombinant cells that express specific cell surface receptors and that have been modified for use in assays that detect compounds that interact with or modulate the activities of cell surface receptors.

SUMMARY OF THE INVENTION

Recombinant cells which are useful for assaying compounds for their agonist or antagonist activity with respect to specific cell surface proteins are provided. The recombinant cells are genetically engineered to express specific ion channels or specific cell surface localized receptors and also contain DNA constructs that include a reporter gene, a promoter region and other transcriptional regulatory sequences of nucleotides that modulate the level of transcription from the promoter. The transcriptional regulatory sequences and/or the promoter region that are selected are regulated, directly or indirectly, by intracellular signals that result from the interaction of the cell surface protein with extracellular signal. Transcription based assay methods that use recombinant cells to detect extracellular signals that act as agonists and antagonists of the activity of the cell surface proteins are also provided.

In particular embodiments, methods for identifying extracellular signals that modulate cell surface protein-mediated transcription are provided. These methods compare the difference in the amount of transcription of a reporter gene in recombinant cells in the presence of the signal, with the amount of transcription in the absence of the signal, or with the amount of transcription in a control cell that does not express the cell surface protein. The recombinant cells used in these methods express the cell surface protein and contain a reporter gene construct in which transcription of the reporter gene is under the control of a promoter transcriptional control sequences whose activity is regulated by the cell surface protein. The recombinant cells may endogenously express the cell surface protein or may express heterologous DNA that encodes the cell surface protein.

In preferred embodiments, the cell surface proteins are cell surface receptors or ion channels. In more preferred embodiments, the cell surface proteins are any of the muscarinic receptors, neuronal nicotinic acetylcholine receptors, gamma-aminobutyric acid (GABA) receptors, glutamate receptors, adrenergic receptors, dopamine receptors, serotonin receptors, and calcium, sodium and potassium ion channels. The promoter region and transcriptional regulatory sequences are any of c-fos gene prompter and the c-fos gene-derived transcriptional regulatory sequences of nucleotides, the vasoactive intestinal peptide (VIP) gene promoter, the somatostatin gene promoter, the proenkephalin promoter, the phosphoenolpyruvate carboxykinase gene promoter and the nerve growth factor-1 A gene promoter. The reporter genes are any of the genes encoding bacterial; chloramphenicol acetyltransferase, firefly luciferase, bacterial luciferase, $\beta$-galactosidase and alkaline phosphatase; and other transcriptional regulatory elements, including cyclic adenosine monophosphate responsive elements, and elements responsive to intracellular calcium ion levels.

In most preferred embodiments, the receptors are muscarinic receptors, and the promoter and other regulatory sequences are derived from the c-fos gene, including the c-fos promoter region and the c-fos gene intragenic regulatory element (FIRE).

Rapid, reliable and sensitive methods to determine if cells are producing specific functional ion channels and cell specific functional surface-localized receptors, including specific receptor and ion channel subtypes are also provided.

The transcription based assays provide rapid, reliable and sensitive means to identify compounds which interact with, and thereby affect the function of specific ion channels and/or specific cell surface-localized receptors. In particular, the assays provide means to screen or detect potential pharmaceutical compounds. Depending upon the affinity of the compound for the cell surface protein or the nature of the interaction, the assays should be able to detect compounds at concentrations in the nanomolar and, possibly, lower range.

In developing the recombinant cells assays, it was recognized that a common thread among concerted tissue responses and cellular responses and activities, such as muscle contraction, vasodilation, cell growth and proliferation, which are mediated by membrane surface proteins, is that transcription of specific genes is initiated rapidly, within minutes of exposure of the cell surface membrane protein to an extracellular signal that induces such activity. Thus, activity of such promoters and transcription of genes controlled by the promoters mirrors the activity of the surface protein by virtue of transduction of an intracellular signal.

The intracellular signal that is transduced is generally initiated by the specific interaction of an extracellular signal, particularly a ligand, with a receptor or ion channel present on the cell surface. This interaction sets in motion a cascade of intracellular events, the ultimate consequence of which is a rapid and detectable change in the transcription or translation of a gene. By selecting promoters that are responsive to the transduced intracellular signals and operatively linking the selected promoters to reporter genes, whose transcription, translation or ultimate activity is readily detectable and measurable, the transcription based assay provides a rapid indication of whether a specific receptor or ion channel interacts with a test compound in any way that influences intracellular transduction. Expression of the reporter gene, thus, provides a valuable screening tool for the development of compounds that act as agonists or antagonists of a cell receptor or ion channel.

The assays of this invention measure the end stage of the above described cascade of events, expression of a reporter gene. This is accomplished through the use of a reporter gene expression construct which contains a reporter gene and a transcriptional control element responsive to the intracellular condition that occurs when the cell receptor or ion channel of a specific type interacts with a compound having agonist or antagonist properties with respect to said receptor or ion channel. The reporter gene is placed in operational association with the transcriptional control element. The appearance of reporter gene product serves as a readily observed indication of transcription.

DESCRIPTION OF THE PREFERRED EMBODIMENTS

Definitions

Unless defined otherwise, all technical and scientific terms used herein have the same meaning as is commonly understood by one of skill in the art to which this invention belongs. All publications mentioned herein are incorporated by reference thereto. All U.S. patents mentioned herein are incorporated in their entirety by reference thereto.

As used herein, recombinant cells include any cells that have been modified by the introduction of heterologous DNA. Control cells include cells that are substantially identical to the recombinant cells, but do not express the one or more of the proteins encoded by the heterologous DNA. For example, the recombinant cells have are produced from cells by the introduction of DNA that encodes are reporter gene construct and also heterologous DNA encoding a cell surface receptor. Control cells, with respect to such recombinant cells, are cells that either do not include or express the reporter gene construct or that do not include or express the receptor.

As used herein, heterologous DNA includes DNA that does not occur naturally as part of the genome in which it is present or which is found in a location or locations in the genome that differs from that in which it occurs in nature. Heterologous DNA is not endogenous to the cell into which it is introduced, but has been obtained from another cell. Generally, although not necessarily, such DNA encodes RNA and proteins that are not normally produced by the cell in which it is expressed. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, DNA that encodes receptors, reporter genes, transcriptional and transnational regulatory sequences, selectable or traceable marker proteins, such as a protein that confers drug resistance.

As used herein, cell surface proteins include molecules that occur on the surface of cells, interact with the extracellular environment, and transmit or transduce the information regarding the environment intracellularly in a manner that ultimately modulates transcription of specific promoters, resulting in transcription of specific genes.

As used herein, extracellular signals include an molecule or a change in the environment that is transduced intracellularly via cell surface proteins that interact, directly or indirectly, with the signal. An extracellular signal or effector molecule is any compound or substance that in some manner specifically alters the activity of a cell surface protein. Examples of such signals include, but are not limited to, molecules such as acetylcholine, growth factors, hormones and other mitogenic substances, such as phorbol mistric acetate (PMA), that bind to cell surface receptors and ion channels and modulate the activity of such receptors and channels. For example, antagonists are extracellular signals that block or decrease the activity of cell surface protein and agonists are examples of extracellular signals that potentiate, induce or otherwise enhance the activity of cell surface proteins.

As used herein, extracellular signals also include as yet unidentified substances that modulate the activity of a cell surface protein and thereby affecting intracellular functions and that are potential pharmacological agents that may be used to treat specific diseases by modulating the activity of specific cell surface receptors.

As used herein receptors that are stimulated by acetylcholine are nicotinic and muscarinic receptors, which can be distinguished from each other by methods known to those of skill in the art. For example, nicotinic and muscarinic receptors can be distinguished based on their response to the alkaloids nicotine and muscarine.

As used herein muscarinic receptors refer collectively to any of the pharmacologically or structurally distinguishable forms of the muscarinic receptors. Any particular form is referred to by any nomenclature recognized by those of skill in the art. For example, pharmacologically defined subtypes have been denoted by a capital M, i.e., $M_1$, $M_2$ and $M_3$, and the distinguishable molecular forms have been denoted by a lower case m, i.e., $m_1$, $m_2$... $m_5$ (see, e.g., Flier et al. (1989) New Engl. J. Med. 321: 1022–1029.

As used herein, a reporter gene construct is a DNA molecule that includes a reporter gene operatively linked to a transcriptional control sequences. Transcription of the reporter gene is controlled by these sequences. The activity of at least one or more of these control sequences is directly or indirectly regulated by the cell surface protein. The transcriptional control sequences include the promoter and other regulatory regions, such as enhancer sequences, that modulate the activity of the promoter, or control sequences that modulate the activity or efficiency of the RNA polymerase that recognizes the promoter, or control sequences are recognized by effector molecules, including those that are specifically induced by interaction of an extracellular signal with a cell surface protein. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional control elements or sequences. In addition, the construct may include sequences of nucleotides that alter translation of the resulting mRNA, thereby altering the amount of reporter gene product.

As used herein, promoter refers to the region of DNA that is upstream with respect to the direction of transcription of the transcription initiation site. It includes the RNA polymerase binding and transcription imitation sites and any other regions, including, but not limited to repressor or activator protein binding sites, calcium or cAMP responsive sites, and any such sequences of nucleotides known to those of skill in the art to alter the amount of transcription from the promoter, either directly or indirectly.

As used herein, a promoter that is regulated or mediated by the activity of a cell surface protein is a promoter whose activity changes when a cell is exposed to a particular extracellular signal by virtue of the presence of cell surface proteins whose activities are affected by the extracellular protein. For example,. the c-fos promoter, which is specifically activated upon the specific interaction of certain extracellular signals, such as growth hormones, with a cell surface protein, such as a growth hormone receptor. In particular, the regulation of such promoters by the cell surface protein, though indirect, occurs within minutes of the interaction of the cell surface protein with the extracellular signal. A s used herein, operative linkage refers to a DNA fragment, such as linkage of a promoter to a DNA molecule that is transcribed by RNA polymerase that binds to the promoter, such that the regulatory region is properly positioned for its activity. Thus, a DNA fragment in operative linkage with a promoter is downstream, with respect to the direction of transcription, from the promoter, is in the correct reading frame with respect to the transcription initiation site and is inserted in a manner such transcription elongation proceeds through the DNA fragment.

The transcription based assay

In practicing the assay, a reporter gene construct is inserted into an eukaryotic cell to produce a recombinant cell which has present on its surface a cell surface protein of a specific type. The cell surface receptor may be endogenously expressed or it may be expressed from a heterologous gene that has been introduced into the cell. Methods for introducing heterologous DNA into eukaryotic cells are-well known in the art and any such method may be used. In addition, DNA encoding various cell surface proteins is known to those of skill in the art or it may be cloned by any method known to those of skill in the art.

The recombinant cell is contacted with a test compound and the level of reporter gene expression is measured. The contacting may be effected in any vehicle and the testing may be by any means using any protocols, such as serial dilution, for assessing specific molecular interactions known to those of skill in the art.

After contacting the recombinant cell for a sufficient time to effect any interactions, the level of gene expression is measured. The amount of time to effect such interactions may be empirically determined, such as by running a time course and measuring the level of transcription as a function of time.

The amount of transcription may be measured using any method known to those of skill in the art to be suitable. For example, specific mRNA expression may be detected using Northern blots or specific protein product may be identified by a characteristic stain.

The amount of transcription is then compared to the amount of transcription in either the same cell in the absence of the test. compound or it may be compared with the amount of transcription in a substantially identical cell that lacks the specific receptors. A substantially identical cell may be derived from the same cells from which the recombinant cell was prepared but which had not been modified by introduction of heterologous DNA. Alternatively, it may be a cell in which the specific receptors are removed. Any statistically or otherwise significant difference in the amount of transcription indicates that the test compound has in some manner altered the activity of the specific receptor.

If the test compound does not appear to enhance, activate or induce the activity of the cell surface protein, the assay may be repeated and modified by the introduction of a step in which the recombinant cell is first tested for the ability of a known agonist or activator of the specific receptor to activate transcription if the transcription is induced, the test compound is then be assayed for its ability to inhibit, block or otherwise affect the activity of the agonist.

The transcription based assay is useful for identifying compounds that interact with any cell surface protein whose activity ultimately alters gene expression. In particular, the assays can be used to test functional ligand-receptor or ligand-ion channel interactions for at least four categories of cell surface-localized receptors which are presently known: ligand-gated ion channels and voltage-gated ion channels, G protein-coupled receptors and growth factor receptors. Examples of each group include:

ligand-gated ion channels: nicotinic acetylcholine receptors, GABA (gamma-aminobutyric acid) receptors, excitatory receptors (e.g., glutamate and aspartate), and the like;

voltage-gated ion channels: calcium channels, potassium channels, sodium channels and the like;

G protein-coupled receptors: adrenergic receptors, muscarinic receptors and the like.

Growth factor receptors: Nerve growth factor NGF, heparin binding growth factors and other growth factors.

The invention assay is also useful for determining functional ligand-receptor interactions in cells containing a NMDA (N-methyl-D-aspartate) receptor, which has recently been categorized as being a ligand-gated, voltage-dependent ion channel.

Preparation of recombinant cells

Any transfectable cell that can express the desired cell surface protein in a manner such the protein functions to intracellularly transduce an extracellular signal may be used. The cells may be selected such that they endogenously express the cell surface protein or may be genetically engineered to do so. Many such cells are known to those of skill in the art. Such cells include, but are not limited to Ltk⁻ cells, PC12 cells and COS-7 cells.

The preparation of cells which express a receptor or ion channel and a reporter gene expression construct, and which are useful for testing compounds to assess their activities, is exemplified in the Examples provided herewith by reference to mammalian Ltk⁻ and COS-7 cell lines, which express the Type I human muscarinic (HM1) receptor and which are transformed with either a c-fos promoter-CAT reporter gene expression construct or a c-fos promoter-luciferase reporter gene expression construct.

Cell surface proteins

Any cell surface protein that is known to those of skill in the art or that may be identified by those of skill in the art may used in the assay. The cell surface protein may endogenously expressed on the selected cell or it may be expressed from cloned DNA.

Exemplary cell surface proteins include, but are not limited to, cell surface receptors and ion channels. Cell surface receptors include, but are not limited to, muscarinic receptors (e.g., human M2 (GenBank accession #M16404); rat M3 (GenBank accession #M16407); human M4 (GenBank accession #M16405); human M5 (Bonner et al. (1988) Neuron 1:403–410); and the like); neuronal nicotinic acetylcholine receptors (e.g., the $\alpha_2$, $\alpha_3$ and $\beta_2$ subtypes disclosed in U.S. Ser. No. 504,455 (filed Apr. 3, 1990), hereby expressly incorporated by reference herein in its entirety); the rat $\alpha 2$ subunit (Wada et al. (1988) Science 240:330–334); the rat $\alpha 3$ subunit (Boulter et al. (1986) Nature 319:368–374); the rat $\alpha 4$ subunit (Goldman et al. (1987) cell 48:965–973); the rat $\alpha 5$ subunit (Boulter et al. (1990) J. Biol. Chem. 265:4472–4482); the rat $\beta 2$ subunit (Deneris et al. (1988) Neuron 1:45–54); the rat $\beta 3$ subunit (Deneris et al. (1989) J. Biol. Chem. 264: 6268–6272); the rat $\beta 4$ subunit (Duvoisin et al. (1989) Neuron 3:487–496); combinations of the rat $\alpha$ subunits, $\beta$ subunits and $\alpha$ and $\beta$ subunits; GABA receptors (e.g., the bovine $\alpha_1$ and $\beta_1$ subunits (Schofield et al. (1987) Nature 328:221–227); the bovine $\alpha_2$ and $\alpha_3$ subunits (Levitan et al. (1988) Nature 335:76–79); the $\gamma$-subunit (Pritchett et al. (1989) Nature 338:582–585); the $\beta_2$ and $\beta_3$ subunits (Ymer et alo (1989) EMBO J. 8:1665–1670); the $\delta$ subunit (Shivers, B.D. (1989) Neuron 3:327–337); and the like); glutamate receptors (e.g., receptor isolated from rat brain (Hollmann et al. (1989) Nature 342:643–648); and the like); adrenergic receptors (e.g., human $\beta 1$ (Frielle et al. (1987) Proc. Natl. Acad. Sci. 84.:7920–7924); human $\alpha 2$ (Kobilka et al. (1987) Science 238:650–656); hamster $\beta 2$ (Dixon et al. (1986) Nature 321:75–79); and the like); dopamine receptors (e.g., human D2 (Stormann et al. (1990) Molec. Pharm.37:1–6); rat (Bunzow et al. (1988) Nature 336:783–787); and the like); NGF receptors (e.g., human NGF receptors (Johnson et al. (1986) Cell 47:545–554); and the like); serotonin receptors (e.g., human 5HT1a (Kobilka et al. (1987) Nature 329:75–79); rat 5HT2 (Julius et al. (1990) PNAS 87:928–932); rat 5HT1c (Julius et al. (1988) Science 241:558–564); and the like).

Ion channels include, but are not limited to, calcium ion channels (e.g., human neuronal $\alpha 2$ subunit (see W089/09834); rabbit skeletal muscle $\alpha 1$ subunit (Tanabe et al. (1987) Nature 328:313-E318); rabbit skeletal muscle $\alpha 2$ subunit (Ellis et al. (1988) Science 241:1661–1664); rabbit skeletal muscle $\beta$ subunit (Ruth et al. (1989) Science 245:1115–1118); rabbit skeletal muscle $\gamma$ subunit (Jay et al. (1990) Science 248:490–492); and the like); potassium ion channels (e.g., rat brain (BK2) (McKinnon, D. (1989) J. Biol. Chem. 264: 8230–8236); mouse brain (BK1) (Tempel et al. (1988) Nature 332:837–839); and the like); sodium ion channels (e.g., rat brain I and II (Noda et al. (1986) Nature 320:188–192); rat brain III (Kayano et al, (1988) FEBS Lett. 228:187–194); and others).

Reporter gene constructs

Reporter gene constructs are prepared by operatively linking a reporter gene with at least one transcriptional regulatory element. If only one transcriptional regulatory element is included it must be a regulatable promoter, At least oneof the selected transcriptional regulatory elements must be indirectly or directly regulated by the activity of the selected cell-surface receptor whereby activity of the receptor can be monitored via transcription of the reporter genes.

The construct may contain additional transcriptional regulatory elements, such as a FIRE sequence, or other sequence, that is not necessarily regulated by the cell surface protein, but is selected for its ability to reduce background level transcription or to amplify the transduced signal and to thereby increase the sensitivity and reliability of the assay.

Many reporter genes and transcriptional regulatory elements are known to those of skill in the art and others may be identified or synthesized by methods known to those of skill in the art.

Reporter genes

A reporter gene includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), Nature 282: 864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1: 4154–4158; Baldwin et al. (1984), Biochemistry 23: 3663–3667); alkaline phosphatase (Toh et al. (1989) Eur. J. Biochem. 182: 231–238, Hall et al. (1983) J. Mol. Appl. Gen. 2: 101).

Transcriptional control elements

Transcriptional control elements include, but are not limited to, promoters, enhancers, and repressor and activator binding sites, Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al. (1990) Neuron 4: 477–485), such as c-fos, Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

In the most preferred constructs, the transcriptional regulatory elements are derived from the c-fos gene.

The c-fos proto oncogene is the cellular homolog of the transforming gene of FBJ osteosarcoma virus. It encodes a nuclear protein that most likely involved in normal cellular growth and differentiation. Transcription of c-fos is transiently and rapidly activated by growth factors and by other inducers of other cell surface proteins, including hormones, differentiation-specific agents, stress, mitogens and other known inducers of cell surface proteins. Activation is protein synthesis independent. The c-fos regulatory elements include (see, Verma et al. (1987) Cell 51: a TATA box that is required for transcription initiation; two upstream elements for basal transcription, and an enhancer, which includes an element with dyad symmetry and which is required for induction by TPA, serum, EGF, and PMA.

The 20 bp transcriptional enhancer element located between −317 and −298 bp upstream from the c-fos mRNA cap site, which is essential for serum induction in serum starved NIH 3T3 cells. One of the two upstream elements is located at -63--57 and it resembles the consensus sequence for cAMP regulation.

Other promoters and transcriptional control elements, in addition to those described above, include the vasoactive intestinal peptide (VIP) gene promoter (cAMP responsive; Fink et al. (1988), Proc. Natl. Acad. Sci. 85:6662-6666); the somatostatin gene promoter (cAMP responsive; Montminy et al. (1986), Proc. Natl. Acad. Sci. 8.3:6682-6686); the proenkephalin promoter (responsive to cAMP, nicotinic agonists, and phorbol esters; Comb et al. (1986), Nature 323:353-356); the phosphoenolpyruvate carboxy-kinase gene promoter (cAMP responsive; Short et al. (1986), J. Biol. Chem. 261:9721-9726); the NGFI-A gene promoter (responsive to NGF, cAMP, and serum; Changelian et al. (1989). Proc. Natl. Acad. Sci. 86:377-381); and others that may be known to or prepared by those of skill in the art.

The following examples are included for illustrative purposes only and are not intended to limit the scope of the invention.

EXAMPLE 1

Preparation of stable and transiently co-transfected mammalian cell lines that express HM1 receptors and that contain DNA encoding a reporter gens under the control of a promoter whose activity is modulated, either directly or indirectly, by HM1 effectors.

Stable cell lines and transiently transfected cell lines for use in the transcription based assay were prepared. Ltk−cells, which are a thymidine kinass deficient mouse fibroblast cell line, were stably cotransfected with a plasmid containing DNA that encodes HM1, a selection plasmid containing either the wild-type or crippled thymidine kinase gene, and a reporter gene expression construct. COS-7 cells (African Green Monkey kidney cells) were transiently co-transfected with a reporter gene construct, and a β-galactosidase expression plasmid, pCH110 (Hall et al. (1983) J. Mol. Appl. Gen. 2: 101), which contains DNA encoding the HM1 receptor.

A. Preparation of mammalian cell lines that have been modified for use in the transcription based assay.

The following cell lines were used as host cells: HEK 293, which are available from ATCC (accession #CRL 1573); LKt−cells, which are available from ATCC (accession #CCL1.3); COS-7 cells, which are available from ATCC (accession #CRL 1651); and DG44 (see, e.g., L. Chasin (1986) Cell. Molec. Genet. 12: 555).

B. DNA that encodes M1 receptor was cloned and inserted into an M1 expression plasmid.

The sequence of the HM1-encoding DNA fragment is described in Allard et al. (1987), Nucl. Acids Res. 15: 10604. It can be prepared by synthesizing the DNA, prepared as described by Allard et al., or it can be isolated by screening a partial human genomic DNA library. It has been isolated by screening a partial human genomic library that contains 2.5–4.5 kb-sized EcoRI fragments in the λgt11 vector, with an oligonucleotide homologous to nucleotides 250-279 of the HM1 gene sequence. Screening conditions employed were as follows:

hybridization: 20% deionized formamide, 5 X Denhardt's, 6 X SSPE, 0.2% SDS, 200 μg/ml sonicated herring sperm DNA, 42° C.

wash: 0.2 X SSPE, 0.2% SDS, 50° C.

A positive clone was identified and confirmed to encode the HM1 receptor by DNA sequencing. The EcoRI insert of that clone was isolated and inserted into the EcoRI site of pIBI24 (International Biotechnologies, Inc., New Haven, CT), yielding clone pIBI24/HM1.

The HM1-encoding fragment of pIBI24/HM1 was modified for insertion into the SV40 promoter-based plasmid pSV2dhfr (see Subramani et al. (1981) Mol. Cell. Biol. 1: 854–864). Fifty nanograms of the 1.97 kb BamHI fragment from pIBI24/HM1 were ligated with 50 ng of BamHI-digested M13mp18. The ligation was transformed into E. coli strain JM103, andAmp$^R$ colonies were selected. Correct plasmid was identified by the presence of a 1.45 KpnI digestion fragment. Template was prepared from this plasmid to introduce an ECoRI site immediately before the initiation codon of the human HM1 coding region. This was accomplished by standard mutagenesis using an oligonucleotide that has the sequence ATG CCCCAGCCCC ACCTT-GAATT CATGAACACT TCAGCC (SEQ ID NO. 1).

The mutagenesis products were transformed into JM103 and screened on plaque lifts with an 18 base oligonucleotide (SEQ ID NO 4). Four of the positive clones were subjected to dideoxy sequencing and all were found to have the correct sequence, i.e., an added EcoRI site immediately 5′ of the 5′ ATG. One of the positive sequence clones, mHM1AChR103, was selected and a second EcoRI site was introduced using oligonucleotide-directed mutagenesis following the human HM1 terminating codon using a 37 nucleotide oligonucleotide (SEQ ID NO 2).

Mutagenesis products were transformed into JM103 and screened on plaque lifts with a 17 base oligonucleotide (SEQ ID NO 3). Positive clones were identified and four were sequence to confirm that the EcoRI site had been introduced and that remainder of the sequence was unaltered. The four sequenced clones had the correct sequence.

One of the sequenced clones, M3HM1AR04, was digested with EcoRI and the 1.4 kb fragment representing the human M1 coding region was gel purified and eluted using DE-81 paper. Sixty nanograms of the 1.4 kb fragment were ligated with 20 ng of EcoRI-digested pUC19. Correct clones were identified by the presence of a 1.2 kb KpnI fragment. one of these was chosen and designated pHM1RO2. The 1.4 kb EcoRI fragment was removed from pHM1RO2 and inserted (38.5 ng) into 50 ng of EcoRI-digested pSV2dhfr. The resulting product was transformed into DH5α (Sambrook et al., *Molecular Cloning*, 2nd ed., Cold Spring Harbor Lab, 1989, p. 10) cells and AmpR colonies were selected. Of the selected colonies those that, upon digestion with EcoRI, yielded fragments of 1.4 and 5.0 kb and, upon digestion with PvuII, yielded fragments of 250, 1150, and 5000 had the plasmids. The final HM1 expression vector was called HM1pSV2dHFR.

C. Preparation of TK+(thymidine kinase) selection plasmids.

Either pThx59 (Zipser et al. (1981) *Proc. Natl. Acad. Sci.* 78:6276–6280),which encodes the wildtype TK gene, or pThx24 (ibid,) which encodes a crippled TK gene was cotransfected into Ltk⁻cells along with the muscarinic receptor-expressing plasmids in order to prepare stably modified Ltk cells that express the cloned HM1 receptor on the cell surfaces.

D. Preparation of reporter gene constructs and expression plasmids containing the constructs.

1. The plasmid pFC4 was used to prepare reporter gene constructs that include the c-fos promoter region.

The reporter gene expression plasmid, pFC4 (Deschamps et al. (1985) Science 230: 1174–1177), which contains the CAT gene under the control of the c-fos gene promoter, was used as source of the c-fos promoter and the CAT reporter gene and was also introduced into Ltk⁻cells by cotransfection with DNA encoding receptors. Briefly, Deschamps et al. describe the preparation of a series of plasmids that contain the human c-fos promoter and varying amounts of upstream sequences. A 2.25 Kb ECORI-NaeI fragment (FCl), from the human c-fos gene (van Straaten et al. (1983) *Proc. Natl. Acad. Sci. USA* 80: 3183), which contains the c-fos promoter and upstream sequence into the vector, pSV2CAT (Gorman et al. (1982) *Mol. Cell Biol.* 2: 1044) in place of the AceI-HindIII fragment in pSV2CAT using HindIII linkers. The resulting plasmid was pFC1. A second plasmid, pFC2, was prepared by isolating the 1.4 Kb NaeI (FC2) fragment from the human c-fos gene upstream region and inserting it using HindIII linkers into pSV2CAT as described for FC1. A series of additional plasmids were generated using by deleting portions of the upstream sequence from FC2. Deletions of SmaI to XhoI and SstII to SstII in FC2 yielded FC3 and FC4, respectively. After the deleted fragments that correspond to the residual flanking sequences and fos promoter were digested with Hind III and separated by gel electrophoresis, they were cloned in the SmaI-HindIII digested DNA in place of the original 1.3 Kb fragment. Deschamps et al. also describes the preparation of constructs FC5-11, -10, -20, -30 and -40 and the corresponding plasmids.

In the constructs described below, unless indicated otherwise, the c-fos promoter region is obtained as the 400 bp fragment from pFC4, which includes a 500 bp insert from the c-fos promoter. The 5'-100 base pair portion is derived from a non-contiguous distal upstream region.

2. The c-los promoter-luciferase reporter gene constructs and plasmids

Plasmids, pFC4XP1 and pFC4XP2 were prepared by inserting the FC4 fragment of pFC4 (Deschamps et al. (1985) Science 230: 1174–1177) into pXP1 and pXP2, which contain firefly luciferase reporter gene constructs (see, Nordeen S.K. (1988) Biotechniques, 6(5):454–457). Plasmids pFC4XP1 and pFC4XP2, include two tandem transcrip-tion/translation termination sequences at the 5' end of the c-fos promoter fragment. The two constructs differ in the placement of the c-fos promoter relative to the luciferase gene. In plasmid pFC4XP1, the c-fos promoter is inserted near the 3' end of the polylinker, with only a 66 bp sequence separating it from the luciferase gene. In plasmid pFC4XP2, the c-fos promoter is placed near the 5' end of the polylinker and there is a 36 bp sequence separating it from the luciferase gene. The resulting luciferase reporter gene-containing expression plasmids, pFC4XP1 and pFC4XP2, are interchangeable and were used to transfect PC12 and COS-7 cells.

3. Other c-los promoter-reporter gene constructs and plasmids that contain various portions of the c-fos promoter region and other transcriptional regulatory elements were prepared The size of the c-fos promoter segment in the reporter gene was altered as a means to maximizing the level of induction of reporter gene expression in receptor-expressing cells transfected with the c-fos promoter-reporter gene construct. Reporter gene constructs containing the c-fos promoter segment used in the c-fos promoter-luciferase reporter gene constructs pFC4XP1 and pFC4XP2, described above, which were employed in the PC12 and COS-7 cell transfections is the FC4 fragment of the cfos promoter from plasmid pFC4. Although it has been demonstrated in a variety of applications that this portion of the c-fos promoter is capable of activating transcription of the c-fos gene in response to elevated levels of cAMP and/or calcium, it was not known if larger or smaller portions of the c-fos promoter are more, less or equally effective in stimulating reporter gene expression in particular receptor-expressing cell lines. To investigate this possibility, c-fos promoter-luciferase reporter gene constructs containing larger (2200 bp) and smaller (350 bp) fragments of the c-fos promoter (obtained from plasmids pFC1 and pFC7, respectively) were assembled and used to transfect PC12 cells that express endogenous rat acetylcholine receptors (nAChRs). The transfected cells were then assayed for carbachol-induced luciferase activities.

In addition to the above two plasmids and constructs, a third plasmid containing a c-fos promoter-luciferase reporter gene construct was prepared which contains the 500 bp FC4 c-fos promoter fragment obtained from pFC4, the luciferase gene coding sequence and the c-fos gene intragenic regulatory element (FIRE), which is a 14-mer palindrome TCCCCGG followed by CCGGGGA (see, Lamb et al. (1990) Cell 6:485–496; see also, Bonnieu et al. (1989) Oncogene 4: 881–888; and Blanchard et al. (1988) Biochimie 70.: 877–884). The plasmids containing these constructs, pFC4XP1FIRE and pFC4XP2FIRE, differ from pFC4XP1 and pFC4XP2 only in that the FIRE sequence has been inserted downstream from the c-fos gene promoter-luciferase reporter gene construct.

Since the FIRE sequence lowers expression of c-fos in uninduced cells, including this sequence in the constructs used in the transcription based assay should reduce the background, noise, level and thereby increase the sensitivity and reliability of the assay.

Other plasmids are constructed in which the FIRE sequence is inserted elsewhere in the reporter gene constructs in order to optimize the reduction in noise level obtained by including this sequence. Since the FIRE sequence is located at the end of the first exon in the c-fos gene and appears to act by promoting premature termination of c-fos transcripts in uninduced cells, constructs containing fusions of the reporter gene and various portions of the c-fos gene are constructed. These fusions include the first exon and FIRE sequence of the c-fos gene and increasing amounts of the intragenic region. The amount of intragenic region is optimized by preparing the constructs and testing them for c-fos expression in the absence of inducer. Those that exhibit the lowest levels of expression in the absence of inducer and the highest level of induced expression, i,e., the highest signal to noise ratio are selected for use in the transcription based assay. The constructs may be introduced into PC12, COS-7 and other suitable receptor-expressing and control cells.

4. Preparation of reporter gene constructs and plasmids containing the somatostatin promoter region a. Somatostatin promoter-CAT reporter gene constructs The reporter gene expression plasmid, pΔ(−71), which contains the CAT gene regulated by the somatostatin gene promoter (see, Montminy, M.R. et al., (1986) *Proc. Nat'l Acad. Sci.* USA 83: 6682–6686), was prepared and was introduced into COS-7 cells.

b. Somatostatin promoter-luciferase reporter gene plasmid

The plasmid, pΔ(−71)XP1, which contains a firefly luciferase reporter gene construct under the control of the pΔ(−71) somatostatin promoter element (see, Montminy, M.R. et al., (1986) *Proc. Nat'l Acad. Sci.* USA 83: 6682–6686) was used to transfect COS-7 cells.

E. Preparation of stable and transient cell lines by co-transfection of mammalian host cells with plasmids containing DNA encoding HM1 and the reporter gene constructs and DNA encoding a selective marker 1. Preparation of stably transfected Ltk− cells.

Stable HM1-expressing cell lines were prepared using calcium phosphate transfection to introduce the plasmid DNA (see, Wigler, et al. (1979), *Proc. Natl. Acad. Sci.* 76:1373–1376). Briefly, Ltk− cells were grown in nonselective medium, D+10, which contains Dulbecco's modified Eagle's medium+10% calf serum, 100 U/ml penicillin, and 100 μg/ml streptomycin, in a 10 cm-sized dish, to 20% confluence. The three circular plasmids, the TK+ plasmid, HM1 containing plasmid, and pFC4 plasmid, were co-precipitated with $CaPO_4$ and added to the cell monolayer.

The vector concentrations were as follows:
Thx24:HM1:pFC4 ; 2μg: 2μg: 2μg/ml
Thx59:HM1:pFC4 ; 0.25 μg: 2 μg:2 μg/ml The final concentration of DNA was adjusted to 20 to 40 μg/ml by adding Ltk− or PVC DNA. The transfected cells were cultured for two days in nonselective medium. After two days, the cells were passed, nonselective media was replaced with HAT medium (D+10+15 μg/ml hypoxanthine+1 μg/ml aminopterin+5 μg/ml thymidine), and the cells were cultured for 10–15 days, during which time the cells were "fed" fresh selective (HAT) medium every 3–4 days. After 10–15 days, colonies or clones appeared which indicated acceptance and expression of at least the plasmid carrying the TK gene. Colonies were transferred into separate wells of a 24-well dish and grown in selective medium for seven days. Individual clones were then transferred into 6-well dishes and grown for another seven days in selective medium. -To provide cells for freezing and subsequent molecular and functional receptor analyses, the individual clones in the 6-well dishes were passed to 100 ml dishes. Two of the resulting cell lines were designated LM1FC4-8 and LM1FC4-15.

2. Transient co-transfection of COS-7 cells

The $CaPO_4$ transfection procedure was used in the transient transfection of COS-7 cells. The protocol employed was that described "Current Protocols in Moleculer Biology", 1, Supplement 14, Section I, Unit 9.1.1-3.1.3 Wiley Interscience Publish (1990).

COS-7 cells, (about $1-2 \times 10^6$ cells) were grown to 20% confluence in Dulbecco's Modified Eagle Medium (Gibco #320–1965 AJ) with 10% Fetal Bovine Serum (Gibco #200–6140 AJ), 1x Pen/Strep (Gibco #600–5140 AG) and 1x MEM Non-Essential Amino Acids (Gibco #320–1140 AG). The three circular plasmids containing the HM1 receptor, TK genes, and reporter genes, were co-precipitated with $CaPO_4$ and added to the cell monolayer. The plasmid concentrations were as follows:
pCH110:HM1pSV2dHFR:pFC4XP1: 5 μg: 5 μg: 0.5 μg/ml
pCH110:HM1pSV2dHFR:pΔ(−71): 5 μg: 5 μg: 1 μg/ml
pCH110:HM1pSV2dHFR:pΔ(−71)XP2: 5 μg: 5 μg: 0.5 μg/ml.

Following transfection, cells were incubated for 24–48 hours in the above Dulbecco's Modified Medium and then assayed for reporter gene expression using the transcription based assay and for β-galactosidase expression as described in Example 3.D., below.

EXAMPLE 2

Preparation of cell lines for use as controls in the transcription based assay

Control cell lines with which to compare the levels of transcription in cells that express the cell surface protein and that include a reporter gene were prepared. Two series of control cell lines were prepared using the transfection and culturing protocols described in Example 1.

The first series of control cells were prepared by cotransfecting Ltk− cells with plasmids containing DNA encoding HM1 and TK+ using the methods and HM1 and TK DNA described in Example 1. The first series of cell lines, including the cell lines, LM159-10 and LM124-3, contain endogenous c-fos genes and were engineered and selected to express cloned HM1 receptors. This first series were prepared to be used as both positive and negative controls in the transcription based assays. They were used as positive controls because they demonstrate that the HM1 receptor was expressed and that activation of the expressed HM1 receptor led to an increase in endogenous c-fos RNA. These cell lines also served as negative controls, since they do not include the pFC4 reporter gene construct, and thus were used to show that CAT mRNA or enzyme activity was not detected in the absence of the pFC4 reporter construct.

The second series of control cell lines was prepared by transiently transfecting COS-7 cells with pFC4XP1 and by co-transfecting Ltk⁻cells with pFC4 and TK+DNAs and selecting TK+clones. Ltk⁻cells, LFC4-3, LFC4-5, LFC4-7, LFC4-8, and LFC4-10 were among the selected positive clones.

This series of Ltk based cell lines, including LCF4-3, LCF4-5, LCF4-7, LCF4-8 and LCF4-11, and the co-transfected COS-7 cells do not express HM1 receptors but contain the reporter gene construct. They have, therefore, been used as positive controls to show CAT mRNA and enzyme activity in response to compounds, which activate the c-fos promoter from the pFC4 construct. This second series of cell lines also served as negative controls in the transcription based assays, since CAT mRNA or luciferase activity were not altered when these cells were contacted with HM1 agonists or antagonists.

Untransfected Ltk⁻cells and Ltk⁻cells transfected with pTHx59 (59-0 cells) were used as additional negative controls to show that HM1 antagonists and agonists do not alter c-fos expression in the absence of HM1 receptors. PC12 cells (ATCC CRL1721 and Michel et al. (1989) Br. J. Pharmacol. 97: 914–920) and SH-SY5Y cells (see, Lambert et al. (1989) Eur. J. Pharmacol. 165: 71–77 and Serra et al. (1988) Neurochem 50: 1513–1521), which express endogenous cell surface receptors, were also used as positive control cell lines in the transcription based assays.

EXAMPLE 3

The cell lines, prepared as described in Example 1, which contain DNA encoding the HM1 receptor and a reporter gene construct, were analyzed to assess the ability of the transcription based assay to detect HM1 agonists and antagonists.

Stably co-transfected Ltk⁻cells were analyzed by northern blot hybridization, binding assays and phosphatidyl inositol hydrolysis assays, as well as by the transcription based assay.

A. Detection and analysis of mRNA transcripts from the DNA that encodes HM1, c-fos, and CAT The cell lines first were analyzed for expression of HM1-encoding RNA. Total RNA was isolated from $1 \times 10^7$ cells and 10–15 μg of each RNA were separated on a 1% agarose-formaldehyde gel, followed by transfer onto nitrocellulose. The northern blot was separately probed with one or more of the following probes: random-primed 1.2 or 1.4 Kb EcoRI fragment from plasmid pSV2HM1, to detect HM1 gene expression; random-primed 788 bp TaqI fragment from plasmid pCaMVCN (Alton et al. (1979) Nature 282: 864) to detect CAT gene expression; and random-primed 1.1 Kb PstI fragment from plasmid p-fos1 (Curran et al. (1982) J. Virol. 44: 674–682) to detect c-fos expression.

The filters were hybridized to the probes in 50% deionized formamide, 5X Denhardt's, 5X SSPE and 100 μg/ml sonicated herring sperm DNA at 42° C. and were washed in 0.2X SSPE/0.2% SDS at 65° C.

The expected sizes of the hybridizing bands on the blots should be about 3 kb for HM1, about 2kb for CAT and about 2.2 kb for c-fos.

B. M1 receptor competitive binding assays detected binding of HM1 agonists and antagonists to HM1 cell surface receptors in the experimental cell lines and in the positive control cell lines, Pc12 and SH-SY5Y (see Example 1).

Approximately $1 \times 10^5$ cells were incubated with 1.4 nM of the antagonist [$^3$HI-N-methyl-scopolamine (NMS) for 1 hr at 37° C. in the absence or presence of various concentrations of agonists, including atropine, pirenzepine, carbamylcholine and scopolamine. Unbound labeled ligand was separated from cell-bound label by filtration of the assay mixture through Whatman GF/C filters, which had been pretreated with polyethyleneimine. The filters were washed with 4 ml of ice-cold assay buffer (144 mM NaCl, 4.7 mM KCl, 1.7 mM KH$_2$PO$_4$, 2.5 mM CaCl$_2$·2H$_2$O, 1.1 mM MgCl$_2$, 10 mM glucose, 10 mM Tris/HCl), dried and analyzed in a scintillation counter to detect the amount of bound $^3$H-NMS. Counts bound in the presence of atropine were subtracted from counts bound in the absence of atropine to determine extent of specific binding.

The results of these competitive binding experiments yielded IC$_{50}$ values for displacement Of specifically bound $^3$H-NMS as follows:

TABLE I

| Cell line | pirenzepine | carbamyl-choline | atropine | scopolamine |
| --- | --- | --- | --- | --- |
| PC12 | 900 nM | 200 μM | 7.0 nM | 5 nM |
| SH-SY5Y | 300 nM | 17 μM | 4.0 nM | 4 nM |
| LM159-10 | 200 nM | 1 mM | 4.5 nM | 2 nM |
| LM124-3 | 200 nM | >1 mM | 1.5 nM | 2 nM |
| LM1FC4-8 | 40 nM | 100 μM | 5.0 nM | 2 nM |
| LM1FC4-15 | 60 nM | 170 μM | 4.0 nM | 3 nM |

These results are in close agreement with those reported by Michel et al. ((1989) Br. J. Pharmacol. 97: 914–920) with respect to the muscarinic pharmacology of PC12 cells. Further, cell lines that were prepared by transfection with DNA encoding HM1, LM159-10 and LM124-3, or DNA encoding HM1 and the c-fos-CAT DNA constructs, expressed HM1 receptors which exhibited the expected pharmacological properties.

C. Phosphatidyl inositol (PI) hydrolysis assay

The protocol that was followed was a modification of that reported in Sevva et al.. (1986), Biochem. Biophys. Res. Comm. 140:160–166 and Peralta et al. (1988), Nature 334:434–437. Briefly, since the activation of the M1 muscarinic receptor by an agonist results in activation of the phosphatidyl inositol (PI) hydrolysis cascade, the functional assay involves labeling of cells with $^3$H-myoinositol for 48 or more hrs. The labeled cells are treated with the muscarinic agonist, carbamylcholine (CCh), in the presence and absence of the muscarinic antagonist, atropine, for one hour. The treated cells are lysed and extracted in chloroform-methanol-water after which the inositol phosphates were separated by ion exchange chromatography and quantified by scintillation counting.

Positive control cells, SH-SY5Y and PC12 cells, negative control cells, the 59-0 cell line, and the recombinant experimental cells, LM159-10, LM124-3, LM1FC4-8 and LM1FC4-15, were plated on 12-well plates (Costar) at a density of $5 \times 10^5$ cells/well and labeled with $^3$H-myo-inositol (3 μCi/well) for 65–70 hrs. The medium was decanted and the wells washed with 1 ml of 2X PI assay buffer (10 mM Hepes, 0.5 mM $CaCl_2$, 1 mM $MgCl_2$, 10 mM LiCl in 500 ml DMEM). The cells were incubated in the presence of various concentrations of agonists, or incubated with agonist in the presence or absence of various concentrations of antagonists, for 60 min at 37° C. Following incubation, the cells were lysed and the Suspension extracted with 3 ml of $CHCl_3$/MeOH (1:1). After centrifugation (3200 rpm for 5 min), the upper aqueous phase was removed and diluted with 2 ml $H_2O$ and centrifuged again. The supernatants were loaded on columns containing 1 ml Dowex $1 \times 8$ AG resin previously equilibrated with 5 mM myo-inositol and washed with 9 ml of 5 mM myo-inositol followed by 8 ml of 60 mM sodium formate, 5 mM sodium borate. All of the inositol phosphates (IP1, IP2, IP3) were eluted together with 6 ml of 0.1 M formic acid, 1M ammonium formate. 3 ml of the eluates were removed and counted with 20 ml scintillation fluid for analysis.

Fold stimulation was determined by the calculating the ratio of cpm in the presence of agonist to cpm in the presence of buffer control.

$EC_{50}$ values for agonist stimulation of PI hydrolysis, were determined by measuring PI hydrolyis at various concentrations of agonist. The cpm measured in the presence of buffer only were subtracted from the cpm measured in the presence of the agonist to yield the amount of PI hydrolysis resulting from the binding of the agonist. The maximum amount of PI hydrolyzed, the maximum response, for each agonist was ascertained and the percent maximum response versus concentration of the agonist was plotted and the $ED_{50}$ value determined from the graph.

$IC_{50}$ values for antagonist inhibition of agonist stimulation of PI hydrolysis was determined by measuring the specific value of PI hydrolysis in the presence of a constant concentration of agonist and various concentrations of antagonist. For each concentration of antagonist, the percentage of the maximum response in the absence of antagonist was plotted as a function of antagonist concentration from which the $IC_{50}$ were determined.

As in the receptor binding assays, SH-SY5Y (Serra et al. (1988) Neurochem 50: 1513–1521) and PC12 (Horowitz, J., J. Neurochem. 53:197–204 (1989) cells were used as positive control systems for activation of the PI hydrolysis pathway by muscarinic agonists and inhibition of the stimulation by muscarinic antagonists. In the positive control cell line SH-SY5Y, treatment with 1 mM carbamylcholine resulted in an approximately 50-fold stimulation of inositol phosphate accumulation, which was blocked by 100 nM atropine. In the PC12 cells, treatment with 1 mM carbamycholine resulted in 27-fold activation. The negative control cell line, 59-0 cells, did not respond to carbamycholine treatment, while the cells transfected with the M1 cDNA displayed varying levels of carbamycholine stimulation. The stimulation observed with 1 mM carbamycholine is summarized below for the positive control and transfected cell lines.

TABLE II

| Cell line | Fold Stimulation | $ED_{50}$, μM |
|---|---|---|
| PC12 | 27 | 7 |
| SH-SY5Y | 48 | 18 |
| LM159-10 | 9 | 90 |
| LM124-3 | 28 | 48 |
| LM1FC4-8 | 30 | 61 |
| LM1FC4-15 | 4 | 48 |

The pharmacological properties of the transfected cell lines, LM124-3, LM159-10, LM1FC4-8, and LM1FC4-15 cells, as well the SH-SY5Y and PC12 cells were characterized by studying the dose-dependent inhibition of carbamycholine-stimulated inositol phosphate accumulation by the muscarinic antagonists atropine, pirenzepine, and scopolamine. The $IC_{50}$ values obtained for the antagonists are tabulated in below:

TABLE III

| Cell line | Pirenzepine | Atropine | Scopolamine |
|---|---|---|---|
| PC12 | 900 μM | >100 nM | ND |
| SHSY5Y | 3.3 μM | 47 nM | 36 nM |
| LM159-10 | 0.5 μM | 13 nM | 31 nM |
| LM124-3 | 0.2 μM | 15 nM | 15 nM |
| LM1FC4-8 | 0.3 μM | 21 nM | 18 nM |
| LM1FC4-15 | ND | 10 nM | ND |

ND = not determined

D. Transcription-based assay

1. The Ltk$^-$ cells that were stably co-transfected with DNA encoding the HM1 receptor and the c-fos promoter-CAT reporter gene construct expressed HM1 receptors and detectable CAT genemRNA and CAT activity when treated with the M1 agonist, carbachol at 100 μM.

The stably co-transfected Ltk$^-$ cells and control cells were grown to 70–80% confluence in 0.5% serum-containing medium for two days prior to assay. This serum starvation step decreases background levels of c-fos promoter transcription. For each cell type to be assayed, groups of three plates of cells were similarly treated. The various treatments included treatment with 100–500 μM carbachol for 15–45 min, treatment with 20% serum for 15–45 min, no treatment, but including swirling as were the others, and treatment with 10 μM atropine for 5 min prior to treatment with carbachol. One plate in each group was incubated for 30–60 min at 37° C., and then used to isolate total RNA for northern analysis (see Example 3.A.). The other two plates were incubated for 5 hr at 37° C. and then assayed for CAT activity.

a. CAT assay to assess reporter gene induction

Protein lysates were prepared by washing the plates with phosphate-buffered saline (PBS) and then lysing cells on the plate in 500 μl 0.25 M Tris HCl pH 7.8, 1% Triton X100. The lysate was transferred to an eppendorf tube and then incubated at 65° C. for 10 min. After spinning the tube for 5 min in a microfuge at 4° C. the supernatant was transferred to fresh tubes and frozen at $-20°$ C. until used in the CAT assay.

Upon thawing, the lysates were assayed in duplicate for protein, 150 μl of cell lysate was used in the CAT assay. 90 μl of $dH_2O$, 0.5 μl 500 mM chloramphenicol, and 10 μl $^{14}$C-acetyl CoA or $^3$H-acetyl CoA were added to the lysate to initiate the reaction, which was incubated for 1–4 hr at 37° C. The reaction was stopped on ice, and 300 μl cold ethyl acetate was added. The tubes were vortexed, spun in a microfuge for 1 min, and 200 μl of the organic phase was transferred to a glass scintillation vial. The 300 μl ethyl acetate extraction was repeated and the organic extracts were combined with 5 ml Econofluor scintillation counting solution. Radioactivity was determined in a scintillation counter.

b. Northern analysis.

The RNA was probed for the presence of c-fos and CAT RNA as described in Example 3.A. CAT-specific RNA of the expected size was detected.

c. Expression of CAT mRNA was induced in cells that express HM1 receptors and blocked by the M1 antagonist attopine The Ltk⁻ cell lines, including LM159-10 and LM124-3, which had been transfected with plasmids containing the HM1 gene, were analyzed for expression of endogenous c-fos RNA after treatment with the cholinergic agonist carbachol or carbachol and atropine, a muscarinic antagonist. If functional HM1 receptors are present on the surface of the cells, the carbachol should interact with the receptor, leading to increased levels of $Ca^{2+}$ and cAMP, and thereby activate the endogenous c-fos gene transcriptional control element so that the c-fos gene should be transcribed at a higher level, which should be detectable at the RNA level, by an induction of endogenous c-fos RNA. Furthermore, the M1 agonist-mediated induction of c-fos, should be blocked by M1 antagonists.

As shown in the table below, these results were achieved in cell lines LM159-10 and LM124-3, indicating that they do express HM1 receptors that are associated with a functional c-fos induction pathway.

TABLE IV

| | c-fos mRNA Induction | | |
|---|---|---|---|
| cell line | no treatment | 100 μM carbachol | 100 μM carbachol + 10 μM atropine |
| LM159-10 | − | +++ | + |
| LM124-3 | − | +++ | + |
| LtK⁻ | − | − | − |

In cells transfected with the HM1 expression vector plus the c-fos-CAT marker plasmid, e.g., LM1FC4-8 and LM1FC4-15, cells expressing functional HM1 receptors likewise show an increase in c-fos mRNA upon interaction with an HM1 agonist. These cells, however, should also demonstrate an increase in CAT-specific RNA and enzyme activity by nature of activation of the c-fos-CAT expression construct. Upon treatment of cell line LM1FC4-15 with the HM1 agonist, carbachol, and also with a general c-fos expression inducer, 20% serum, increases in c-fos mRNA and CAT mRNA were detected.

TABLE V

| Cell line | no treatment | 100 μM carbachol | 20% serum |
|---|---|---|---|
| LM1FC4-8 | | | |
| c-fos RNA | − | − | + |
| CAT RNA | + | + | + |
| CAT activity | + | + | + |
| LM1FC4-15 | | | |
| c-fos RNA | − | ++ | ++ |
| CAT RNA | + | ++ | ++ |
| CAT activity | + | ++ | ++ |
| LFC4-7 (neg. control) | | | |
| c-fos RNA | − | − | + |
| CAT RNA | + | + | ++ |
| CAT activity | + | + | ++ |

2. COS-7 cells transiently co-transfected with HM1 receptor DNA and reporter gene constructs expressed functional HM1 receptors and increased reporter gene expression a. COS-7 cells transiently co-transfected with HM1 receptor DNA and pFC4XP1

Twenty-four to 48 hours after transient cotransfection of COS-7 cells with the HM1 receptor DNA, c-fos promoter-luciferase reporter gene construct (pFC4XP1) and β-galactosidase gene (pCH110), the transfectants were exposed to 500 μM carbamycholine or untreated for 5 hours. Three to five hours after drug treatment, the cells were lysed and analyzed for luciferase (see, Brasier et al. (1989) Biotechniques, 7:1116–11223), β-galactosidase (Miller (1972), "Experiments in Molecular Genetics" Cold Springs Harbor Laboratory, Cold Spring Harbor, NY) and protein concentration [Biorad] Bradford (1976) Analytical Biochemistry, 72: 248). The concentrations of β-galactosidase and protein were used to normalize luciferase levels to transfection efficiency and protein yield per plate. Normalized luciferase = luciferase activity/$\Delta A420$(β-galactosidase activity)/μg protein/μl, where volumes used for luciferase and β-galactosidase are constant for all lysates. The results are set forth in TABLE VI.

These results indicate that the luciferase levels of COS-7 cells co-transfected with the HM1 receptor DNA and the c-fos promoter-luciferase gene and exposed to 500 μM carbamycholine were 10-fold higher than those of untreated transfectants. The luciferase levels of COS-7 cells that were transfected with pFC4XP1 were not affected by carbamycholine. These data confirm that the luciferase inductions in these cells were HM1 receptor expression specific.

The transcription-based assay has also been used to generate muscarinic acetylcholine receptor agonist and antagonist dose-response curves. Fourteen 10-cm plates of COS-7 cells were transiently co-transfected by the calcium phosphate protocol (see Example I.F.) with HM1pSV2dHFR, pFC4XP1, and pCH110. Forth-eight hours after transfection, duplicate plates of cells were treated with either 0, 0.01, 0.10, 1.0, 10, 100 or 1000 μM carbamycholine for 5 hours prior to lysis of the cells and assaying for carbamycholine-induced luciferase activity. Carbamycholine dose-response luciferase induction was observed over a range of 1 to 1000 μM carbamycholine.

TABLE VI

| COS-7 Transfectant | Luciferase Activity (RLU)[a] | β-gal (ΔA420)[b] μg Protein/μl | Normalized[c] Luciferase Activity (RLU) | Average Luciferase[d] | Luciferase induction (Aug. Luc. + CCh/ Avg. Luc—CCH) |
|---|---|---|---|---|---|
| HM1pSV2dHFR FC4XP1 pCH110 | | | | | |
| —CCh | 75,111 | 0.063 | 1,192,238 | 1,819,737 | |
| —CCh | 176,201 | 0.072 | 2,447,236 | | |
| +CCh | 998,731 | 0.057 | 17,521,596 | 18,945,507 | 10.4 |
| +CCH | 1,120,318 | 0.055 | 20,369,418 | | |
| pFC4XP1 pCH110 | | | | | |
| +CCh | 201,382 | 0.198 | 1,017,080 | | 0.6[e] |
| +CCH | 299,789 | 0.276 | 1,086,192 | 1,065,428 | |

[a]RLU-Relative light units of lysates (100 μl) of the indicated transfected cell samples.
[b]Determined by measuring the change in absorbance of cell lysate samples at 420 nm in the presence of ONPG and dividing by the protein concentration of the lysate.
[c]In order to account for differences in the efficiency of transfection of each plate of cells, the luciferase activity of each cell lysate sample in RLU N was divided by the β-galactosidase level (ΔA$_{420}$) of each lysate sample to obtain luciferase activities normalized in terms of the β-galactosidase levels of the cell sample per μg protein per μl of lysate. This column lists the normalized values of the luciferase activities.
[d]Average of the normalized luciferase activities of duplicate samples of CCh-treated and untreated cells.

[e]This ratio was calculated as follows: $\dfrac{\text{Average luciferase activity of COS-7 cells transfected with pFC4XP1 and exposed to CCh}}{\text{average luciferase activity of untreated COS-7 cells co-transfected with HM1pSV2dHFR and pFC4XP1}}$ An approximate EC$_{50}$ value (6 μM) was calculated from these data. This EC$_{50}$ value correlates with published EC$_{50}$ values for carbamycholine induction of PI hydrolysis in HEK 293 cells transfected with the HM1 receptor gene (see, Peralta el al. (1988), Nature 334:434–437).

Curves for the dose response of atropine inhibition of carbamycholine-induced luciferase activities in transiently co-transfected COS-7 cells have also been generated using the tranScription-based assay. For these experiments, 16 10-cm plates of COS-7 cells were transiently co-transfected by the calcium phosphate protocol with pCH110, HM1pSV2dHFR and pFC4XP1. Fortyeight hours after transfection, duplicate plates of cells were incubated for 5 minutes in either 0, 0.01, 0.1, 1.0, 10, 100, 1,000 or 10,000 nM atropine in STBS (Tris buffered saline) buffer prior to the addition of 500 μM carbamycholine to the plates. After 5 minutes of incubation of the cells in the presence of carbamycholine and atropine, the drugs were removed from the cells and replaced with conditioned media. Five hours after the addition of carbamycholine, cell lysates were made and analyzed for β-galactosidase and luciferase activities and total protein levels.

Atropine inhibited the carbamycholine-induced levels of luciferase in a dose-dependent manner in a range of concentrations from 10–10,000 nM. Because the inhibition of carbamycholine-induced luciferase activity was complete in the presence of 10,000 nM atropine in this experiment (i.e., the luciferase level of cells treated with 500 μM carbamycholine and 10,000 nM atropine was equivalent to that of cells that were not treated with carbamycholine), an IC$_{50}$ of 80 mM for atropine inhibition of was calculated from these data. This IC$_{50}$ value is within range of that determined in assays of atropine inhibition of carbamycholine-induced PI hydrolysis in Ltk−cells transfected with the HM1 receptor gene.

b. COS-7 cells transiently co-transfected with a plasmid containing DNA encoding the HM1 receptor DNA and with a plasmid containing the somatostatin promoter-CAT gene construct COS-7 cells were transiently co-transfected with the somatostatin promoter-CAT gene (pΔ-71) and the HM1 receptor DNA using the calcium phosphate method. Forty-eight hours after transfection,. the cells were either treated with 0.500-1 μM carbamycholine or untreated and incubated for 5 hours. Following the incubation, the cells were assayed for CAT activity as described in Example 3.D. Untransfected, untreated C0S-7 control cells displayed a high background level of CAT activity. The CAT levels of the transfected COS-7 cells that had not been exposed to carbamycholine were equivalent to those of the control cells. The CAT levels of carbamycholine-treated transfected COS-7 cells were approximately 1.7-fold higher than those of the untreated transfected cells.

c. PC12 cells transiently co-transfected with the HM1 receptor DNA and the c-fos promoter-luciferase gene PC12 cells were transiently transfected with 0.5 μg of pFC4XP1 using the calcium phosphate precipitation method. Forty-eight hours after transfection, cells were either exposed to 500 μM carbamycholine or untreated for 5 hours. Cell lysates were prepared and assayed for luciferase activity as described in Example 3. D. (see, Brasier et al. (1989) Biotechniques, 7:1116–1122). The results of these assays indicated that the luciferase level of the carbamycholine-treated cells was 30-fold higher than the luciferase level of the untreated cells.

d. PC12 cells co-transfected with DNA encoding HM1 receptors and with plasmids that contain c-fos-luciferase reporter gene constructs that include various portions of the c-los promoter region Lamb et al. ((1990) Cell 61: 485–496) demonstrated that the FIRE sequence, when inserted into the coding sequence of a c-fos promoter-β-galactosidase fusion gene, reduces constitutive or uninduced levels of c-fos promoter-regulated β-gal transcription. Therefore, cells transfected with a c-fos promoter (pFC4 fragment)-luciferase gene construct containing the FIRE sequence should exhibit lower levels of constitutively expressed, uninduced luciferase activities (noise) than cells transfected with a c-fos promoter-luciferase reporter gene lacking the FIRE sequence. Lower background luciferase levels should, in turn, result in higher signal-to-noise ratios (i.e., the ratio of luciferase activities of carbamycholine-treated and untreated cells) generated in luciferase induction assays of the reporter gene-transfected cells.

PC12 cells were used to analyze the carbachol induction of the three c-fos promoter-luciferase gene constructs, pFC4X2FIRE, pFC1XP2, which includes a 2200 bp c-fos fragment of c-fos and, pFC7XP2, which includes a 350 bp, fragment of the c-fos promoter. For purposes of comparison, PC12 cells were also transfected with pFC4XP2, a plasmid containing a reporter fusion gene consisting of the 500 bp fragment of the c-fos promoter from pFC4 and the coding sequence of the luciferase gene.

The signal-to-noise ratios of the luciferase activities of carbachol-treated versus untreated PC12 cells transfected with the three alternative c-fos promoter-luciferase gene plasmids and the unmodified c-fos promoter-luciferase construct, pFC4XP2 were measured. Carbachol-induced luciferase levels of PC12 cells transfected with the unmodified reporter gene construct pFC4XP2 and the FIRE sequence-containing reporter fusion gene construct (pFC4XP2FIRE) were approximately 12- and 17-fold higher, respectively, than the background luciferase levels of untreated cells. The luciferase levels of carbachol-treated PC12 cells that had been transfected with reporter gene constructs containing larger (pFC1XP2) and smaller (pFC7XP2) c-fOs promoter fragments were 14- and 11-fold higher than the background luciferase levelS, respectively.

Since an improvement in the carbachol induction of luciferase activity was achieved in PC12 cells transfected with the FIRE sequence-containing c-fos promoter-luciferase gene construct, pFC4XP2FIRE, should be possible to achieve improved induction and higher signal to noise ratios by modifying the construct and optimizing the location of the FIRE sequence in the construct with respect to these parameters. The signal-to-noise ratio and, thus, the sensitivity and reliability of the assay should improve when PC12, COS-7 or other cells are transfected with these plasmids and used in the transcription based assay.

In particular, constructs in which the location of the FIRE sequence more closely mimics its location in the c-fos gene are expected to yield improved levels of inductions and signal to noise ratios. For examples, constructs containing a reporter gene fusion that includes at least the first exon of the c-fos gene, including the FIRE sequence, and possibly all or a portion of the intragenic region, should exhibit a relatively high signal to noise ration upon induction of the c-fos promoter region. A series of constructs containing various portions of the c-fos gene can be constructed and fused to a reporter gene and operably linked to the c-fos promoter. COS-7, PC12 cells or other suitable cells can be appropriately transfected and the levels of induction of the reporter gene measured. Any other reporter gene that functions as a reporter gene, such as the gene encoding β-galactosidase, when fused to a portion of the c-fos promoter can be used.

Since modifications will be apparent to those of skill in the art, it is intended that this invention be limited only by the scope of the appended claims. Various features of the invention are also described in the following claims.

What is claimed is:

1. A method for identifying extracellular signals that modulate cell surface protein-mediated activity, comprising:
    comparing the difference in the amount of transcription of a reporter gens in a recombinant cell in the presence of the signal with the amount of transcription in the absence of said signal, or with the amount of transcription in the absence of the cell surface protein, wherein:
    the recombinant cell contains a reporter gens construct and expresses the cell surface protein; and
    transcription of the reporter gens is under the control of at least one transcriptional control element whose activity is regulated by the cell surface protein.

2. The method of claim 1, wherein said protein is a cell surface receptor or ion channel.

3. The method of claim 2, wherein said signal is an agonist or antagonist of said cell surface receptor or ion channel.

4. The method of claim 3, wherein the concentration of said agonist or antagonist is less than 100 μM.

5. The method of claim 3, wherein the concentration of said agonist or antagonist is less than 10 μM.

6. The method of claim 3, wherein the concentration of said agonist or antagonist is less than 1 μM.

7. The method of claim 3, wherein the concentration of said agonist or antagonist is less than 0.1 μM.

8. The method of claim 3, wherein the concentration of said agonist or antagonist is less than 10 nM.

9. The method of claim 3, wherein the concentration of said agonist or antagonist is less than 1 nM.

10. The method of claim 3, wherein the concentration of said agonist or antagonist is less than 0.1 nM.

11. The method of claim 3, wherein the concentration of said agonist or antagonist is less than 0.01 nM.

12. The method of claim 1, wherein the amount of transcription is determined by measuring the amount of mRNA that is transcribed from said reporter gene.

13. The method of claim 1, wherein the amount of transcription is determined by measuring the amount of reporter gene protein that is produced.

14. The method of claim 3, wherein said signal is an antagonist.

15. The method of claim 14, further comprising, prior to or simultaneously with comparing the difference in the amount of transcription of the reporter gene, contacting the recombinant cell with an agonist that activates said cell surface protein, whereby transcription of said reporter gene is induced.

16. The method of claim 1, wherein said reporter gene construct includes transcriptional regulatory sequences of nucleotides that modulate transcription from said transcriptional control element in the absence of said cell surface protein or extracellular signal.

17. The method of claim 16, wherein said transcriptional regulatory sequence is the c-fos gene intragenic regulatory element, whereby the level of transcription of said reporter gene in the absence of said cell surface protein or extracellular signal is less than in the absence of the the intragenic regulatory element.

18. The method of claim 1, wherein the cell surface protein is a cell surface receptor selected from: muscarinic receptors, neuronal nicotinic acetylcholine receptors, gamma-aminobutyric acid receptors, glutamate receptors, adrenergic receptors, dopamine receptors, nerve growth factor receptors, or serotonin receptors.

19. The method of claim 1, wherein the cell surface protein is an ion channel selected from: calcium ion channels, potassium ion channels, or sodium ion channels.

20. The method of claim 1, wherein the transcriptional control element is a promoter selected from: the c-fos gene promoter, the vasoactive intestinal peptide gene promoter, the somatostatin gene promoter, the proenkephalin promoter, the phosphoenolpyruvate carboxykinase gene promoter or the nerve growth factor-1 A gene promoter.

21. The method of claim 1, wherein the reporter gene is selected from: the gene encoding bacterial chloramphenicol acetyltransferase, the gene encoding firefly luciferase, the gene encoding bacterial luciferase, the gene encoding $\beta$-galactosidase or the gene encoding alkaline phosphatase.

22. The method of claim 1, wherein the gene construct includes at least one transcriptional regulatory sequence of nucleotides selected from the group consisting of serum responsive elements, cyclic adenosine monophosphate responsive elements, and elements responsive to intracellular calcium ion levels.

23. The method of claim 18, wherein said receptor is the Type 1 human muscarinic receptor, said transcriptional control element is the c-fos promoter and said reporter gene is the gene encoding bacterial chloramphenicol acetyltransferase.

24. A recombinant cell, comprising:
DNA that encodes a heterologous cell surface protein whose activity is modulated by extracellular signals; and
a reporter gene construct containing a reporter gene in operative linkage with one or more transcriptional control element that is regulated by said cell surface protein.

25. The cell of claim 24, wherein said cell is a PC12 cell or a COS-7 cell that has been modified by introduction of said DNA and reporter gene construct.

26. The cell of claim 25, wherein said reporter gene construct includes transcriptional regulatory sequences of nucleotides that modulate transcription from said promoter in the absence of said cell surface protein or extracellular signal.

27. The cell of claim 26, wherein said transcriptional regulatory sequence is the c-fos gene intragenic regulatory element, which is inserted downstream, with respect to the direction of transcription, from the transcription binding and initiation site of said promoter.

28. The cell of claim 27, wherein said reporter gene construct is FC4XP1FIRE or FC4XP2FIRE.

29. The cell of claim 27, wherein said reporter gene is fused to a sufficient portion of the c-fos gene first exon and intragenic region to reduce the level of transcription of said reporter gene in the absence of said cell surface protein or signal to levels that are substantially undetectable; and
said c-fos gene intragenic regulatory element is inserted in reading frame at the 3' end of the first exon of said c-fos gene.

30. The recombinant cell of claim 24, wherein said cell surface proteins are receptors selected from: muscarinic receptors, neuronal nicotinic acetylcholine receptors, gamma-aminobutyric acid receptors, glutamate receptors, adrenergic receptors, dopamine receptors, nerve growth factor receptors, or serotonin receptors.

31. The recombinant cell of claim 24, wherein said cell surface proteins are ion channels selected from: calcium ion channels, potassium ion channels, or sodium ion channels.

32. The recombinant cell of claim 24, wherein said transcriptional control element is selected from: the c-fos gene promoter, the vasoactive intestinal peptide gene promoter, the somatostatin gene promoter, the proenkephalin promoter, the phosphoenolpyruvate carboxykinase gene promoter, or the nerve growth factor-1 A gene promoter.

33. The recombinant cell of claim 24, wherein said reporter gene is selected from: the gene encoding bacterial chloramphenicol acetyltransferase, the gene encoding firefly luciferase, the gene encoding bacterial luciferase, the gene encoding $\beta$-galactosidase or the gene encoding alkaline phosphatase.

34. The recombinant cell of claim 30, wherein said receptor is Type 1 human muscarinic receptor, said transcriptional control element is the c-fos gene promoter and said reporter gene is the gene encoding bacterial chloramphenicol acetyltransferase.

35. The method of claim 1, wherein said cell surface protein is an ion channel and prior to comparing the difference in the amount of transcription the cell is depolarized.

36. The method claim 1, wherein said cell surface protein is an ion channel and said signal causes depolarization of the cell membrane.

37. A method for identifying compounds that modulate cell surface protein-mediated activity by detecting intracellular transduction of a signal generated upon interaction of the compound with a cell surface protein, comprising:
comparing the amount of transcription of a reporter gene or the amount of reporter gene product expressed in a first recombinant cell in the presence of the compound with the amount of transcription or product in a second recombinant cell; and
selecting compounds that change the amount of transcription of a reporter gene or the amount of reporter gene product expressed in the first recombinant cell in the presence of the compound compared to the amount of transcription or product in the absence of the compound, or compared to the amount of transcription or product in the second recombinant cell, wherein:
the first recombinant cell contains a reporter gene construct and expresses the cell surface protein;
the second recombinant cell is identical to the first recombinant cell, except that it does not express the cell surface protein; and
the reporter gene construct contains:
(a) a transcriptional control element that is responsive to the intracellular signal that is generated by the interaction of an agonist with the cell surface protein; and
(b) a reporter gene that encodes a detectable transcriptional or translational product and that is in operative association with the transcriptional control element. Transcription based assays that identify extracellular signals that modulate the activity of cell surface proteins are provided. Extracellular signals are identified by measuring the amount of transcription of a reporter gene in a recombinant cell that expresses the cell surface protein and contains DNA encoding the reporter gene under the transcriptional control of a promoter that is regulated, directly or indirectly, by the cell surface protein. The assays, provide a means for identifying potential pharmaceutical compounds that can be used to treat disease by virtue of their agonistic or antagonistic effects on the cell surface protein. Recombinant cells that express cell surface receptors and that contain reporter gene constructs that include transcriptional regulatory elements that are responsive to the activity of the cell surface receptors are also provided.

38. The method of claim 37, wherein the compound is an agonist or antagonist of said cell surface receptor or ion channel.

39. The method of claim 37, wherein the amount of transcription is determined by measuring the amount of mRNA that is transcribed from said reporter gene.

40. The method of claim 37, wherein the amount of transcription is determined by measuring the amount of reporter gene protein that is produced.

41. The method of claim 37, further comprising, prior to or simultaneously with comparing the difference in the amount of transcription of the reporter gene, contacting the recombinant cell with an agonist that activates said cell surface protein, whereby transcription of said reporter gene is induced.

42. The method of claim 41, wherein said compound is an antagonist.

43. The method of claim 15, wherein said compound is an antagonist.

44. The method of claim 1, wherein transcription is assessed by measuring the activity of the reporter gene protein.

45. The method of claim 1, wherein the cell is preincubated with the extracellular signal prior to comparing the difference in transcription.

46. The method of claim 45, wherein the cell is contacted with an agonist when comparing the difference in transcription.

47. The method of claim 37, wherein the cell is preincubated with the compound prior to comparing the difference in transcription.

48. The method of claim 47, wherein the cell is contacted with an agonist when comparing the difference in transcription.

* * * * *

UNITED STATES PATENT AND TRADEMARK OFFICE
CERTIFICATE OF CORRECTION

PATENT NO.: 5,436,128

DATED: July 25, 1995

INVENTOR(S): HARPOLD, Michael M.; and BRUST, Paul

It is certified that error appears in the above-identified patent and that said Letters Patent is hereby corrected as shown below:

at column 1, line 27, FIELD OF INVENTION, between "evaluating" and "properties", replace "thepharmacological" with —the pharmacological—.

at column 2, line 20, BACKGROUND OF INVENTION, after "(1990)", replace "Neuron 4:" with the italicized —*Neuron 4:*—.

at column 2, line 67, BACKGROUND OF INVENTION, Sodium channels, after "into", replace "Xenopus" with the italicized —*Xenopus*—.

at column 2, line 68, BACKGROUND OF INVENTION, Sodium channels, after (1986), replaced "Nature" with the italicized —*Nature*—.

at column 3, line 4, BACKGROUND OF INVENTION, Calcium channels, after "entry of", replace "—$Ca^{+2}$" with — $Ca^{2+}$ —.    at column 3, line 11, BACKGROUND OF INVENTION, Calcium channels, after "influx of" replace "—$Ca^{+2}$—" with — $Ca^{2+}$ —.

at column 3, line 59, BACKGROUND OF INVENTION, Ligand-gated ion channels, after "(1987)" replace "science" with the italicized and capitalized —*Science*—.

Column 4, line 5, BACKGROUND OF INVENTION, Ligand-gated ion channels, after "extracellular", replace "—$Ca^{+2}$" with — $Ca^{2+}$ —.

at column 5, line 8, BACKGROUND OF INVENTION, G-coupled receptors, between "slime mold," and "is induced", replace "Dictyostelium, " with the italicized —*Dictyostelium,* —.

at column 6, line 44, BACKGROUND OF INVENTION, The c-fos Gene and Related Genes, between "influx of" and "ions", replace "—$Ca^{2+}$—" with — $Ca^{2+}$ —.

UNITED STATES PATENT AND TRADEMARK OFFICE
CERTIFICATE OF CORRECTION

PATENT NO.: 5,436,128

DATED: July 25, 1995

INVENTOR(S): HARPOLD, Michael M.; and BRUST, Paul

It is certified that error appears in the above-identified patent and that said Letters Patent is hereby corrected as shown below:

at column 6, line 45, BACKGROUND OF INVENTION, The c-fos Gene and Related Genes, before channels, replace "—$Ca^{2+}$—" with — $Ca^{2+}$ —.

at column 9, line 16, SUMMARY OF THE INVENTION, between "activity" and "readily", replace "iS" with —is—.

at column 11, line 38, DESCRIPTION OF THE PREFERRED EMBODIMENTS, Definitions, between "signal." and "used herein,", replace "A s" with —As—.

at column 15, line 68, DESCRIPTION OF THE PREFERRED EMBODIMENTS, EXAMPLE 1, between "thymidine" and "deficient", replace "kinass" with —kinase—.

at column 18, line 13, DESCRIPTION OF THE PREFERRED EMBODIMENTS, D. Preparation of reporter gene constructs and expression plasmids containing the constructs., between "2. The" and "promoter", replace " c-los " with — c-fos —.

at column 18, line 35, DESCRIPTION OF THE PREFERRED EMBODIMENTS, D. Preparation of reporter gene constructs and expression plasmids containing the constructs., between "3. Other" and "promoter", replace " c-los " with — c-fos —.

at column 21, line 41, DESCRIPTION OF THE PREFERRED EMBODIMENTS, EXAMPLE 2, after "(1988)", replace "Neurochem 50:" with the italicized —*Neurochem 50:*—.

at column 21, line 68, DESCRIPTION OF THE PREFERRED EMBODIMENTS, EXAMPLE 3, after "(1979)", replace "Nature 282:" with the italicized —*Nature 282:*—.

UNITED STATES PATENT AND TRADEMARK OFFICE
CERTIFICATE OF CORRECTION

PATENT NO.: 5,436,128

DATED: July 25, 1995

INVENTOR(S): HARPOLD, Michael M.; and BRUST, Paul

It is certified that error appears in the above-identified patent and that said Letters Patent is hereby corrected as shown below:

at column 22, line 14, DESCRIPTION OF THE PREFERRED EMBODIMENTS, EXAMPLE 3, between "lines," and "and SH-SY5Y", replace "Pc12" with —PC12—.

at column 23, line 54, DESCRIPTION OF THE PREFERRED EMBODIMENTS, C. Phosphatidyl inositol (PI) hydrolysis assay, after "(1988)", replace "Neurochem 50:" with the italicized —*Neurochem 50:*—.

at column 28, line 48, DESCRIPTION OF THE PREFERRED EMBODIMENTS, D. Transcription-based assay, after "(1989)", replace "Biotechniques 7:" with the italicized —*Biotechniques 7:*—.

at column 28, line 56, DESCRIPTION OF THE PREFERRED EMBODIMENTS, D. Transcription-based assay, between "portions of the" and "promoter", replace " c-los " with — c-fos —.

at column 29, line 29, DESCRIPTION OF THE PREFERRED EMBODIMENTS, D. Transcription-based assay, between "(pFC7XP2)" and "promoter", replace " c-fOs " with — c-fos —.

IN THE CLAIMS at column 30, line 5, claim 1, after "reporter", replace "gens" with —gene—.

at column 30, line 10, claim 1, after "reporter", replace "gens" with —gene—.

UNITED STATES PATENT AND TRADEMARK OFFICE
CERTIFICATE OF CORRECTION

PATENT NO.: 5,436,128

Page 4 of 4

DATED: July 25, 1995

INVENTOR(S): HARPOLD, Michael M.; and BRUST, Paul

It is certified that error appears in the above-identified patent and that said Letters Patent is hereby corrected as shown below:

at column 30, line 12, claim 1, after "reporter", replace "gens" with —gene—.

at column 32, line 59, claim 37, after "element", delete the four sentences "Transcription based assays that identify extracellular signals that modulate the activity of cell surface proteins are provided. Extracellular signals are identified by measuring the amount of transcription of a reporter gene in a recombinant cell that expresses the cell surface protein and contains DNA encoding the reporter gene under transcriptional control of a promoter that is regulated, directly or indirectly, by the cell surface protein. The assays, provide a means for identifying potential pharmaceutical compounds that can be used to treat disease by virtue of their agonistic or antagonist effects on the cell surface protein. Recombinant cells that express cell surface receptors and that contain reporter gene constructs that include transcriptional regulatory elements that are responsive to the activity of the cell surface receptors are also provided."

Signed and Sealed this

Twenty-sixth Day of March, 1996

Attest:

BRUCE LEHMAN

*Attesting Officer*　　*Commissioner of Patents and Trademarks*

UNITED STATES PATENT AND TRADEMARK OFFICE
CERTIFICATE OF CORRECTION

PATENT NO. : 5,436,128            Page 1 of 2
DATED       : July 25, 1995
INVENTOR(S) : Harpold et al.

It is certified that error appears in the above-indentified patent and that said Letters Patent is hereby corrected as shown below:
On the title page;

in the Date of the Patent, on the front page, second column, line 2, before "Jul.", add a —*—;

between the Assignee and the Application Number, on the front page, first column, line 12, add —    [*]     Notice:     The portion of the term of this patent subsequent to March 28, 2012 has been disclaimed.—;

UNITED STATES PATENT AND TRADEMARK OFFICE
CERTIFICATE OF CORRECTION

PATENT NO. : 5,436,128
DATED : July 25, 1995
INVENTOR(S) : Harpold et al.

It is certified that error appears in the above-indentified patent and that said Letters Patent is hereby corrected as shown below:

delete Claim 43 and renumber the following Claims 44 to 48 as Claims 43 to 47;

in Claim 46, now renumbered Claim 45, column 34, line 13, between "claim" and "wherein", change "45," to —44,—; and in Claim 48, now renumbered Claim 47, column 34, line 19, between "claim" and "wherein", change "47," to —46,—.

Signed and Sealed this

Twenty-second Day of October, 1996

Attest:

BRUCE LEHMAN

*Attesting Officer*  *Commissioner of Patents and Trademarks*

Disclaimer 5,436,128—Michael M. Harpold, El Cajon; Paul Brust, San Diego, both of Calif. ASSAY METHODS AND COMPOSITIONS FOR DETECTING AND EVALUATING THE INTRACELLULAR TRANSDUCTION OF AN EXTRACELLULAR SIGNAL. Patent dated July 25, 1995. Disclaimer filed January 25, 2001, by the assignee, Merck & Co., Inc.

Hereby enters this disclaimer to claims 1-47 of said patent.
*(Official Gazette, June 5, 2001)*